(12) United States Patent
Mingione et al.

(10) Patent No.: US 11,832,880 B2
(45) Date of Patent: Dec. 5, 2023

(54) ENERGY DELIVERY DEVICES AND RELATED SYSTEMS AND METHODS THEREOF

(71) Applicant: NeuWave Medical, Inc., Madison, WI (US)

(72) Inventors: Louie Mingione, Madison, WI (US); Mark Thom, Madison, WI (US)

(73) Assignee: NeuWave Medical, Inc., Madison, WI (US)

( * ) Notice: Subject to any disclaimer, the term of this patent is extended or adjusted under 35 U.S.C. 154(b) by 991 days.

(21) Appl. No.: 16/714,063

(22) Filed: Dec. 13, 2019

(65) Prior Publication Data
US 2020/0188022 A1    Jun. 18, 2020

Related U.S. Application Data

(60) Provisional application No. 62/779,299, filed on Dec. 13, 2018.

(51) Int. Cl.
*A61B 18/18* (2006.01)
*A61B 18/00* (2006.01)

(52) U.S. Cl.
CPC ...... *A61B 18/1815* (2013.01); *A61B 2018/00017* (2013.01); *A61B 2018/00577* (2013.01);
(Continued)

(58) Field of Classification Search
CPC ........... A61B 18/18; A61B 18/1815; A61B 2018/00577; A61B 2018/00982; A61B 2018/1838; A61B 2018/1869; A61B 2018/00107; A61B 2018/1823; A61B 2018/1861; A61B 2018/1846; A61B 2018/1853
(Continued)

(56) References Cited

U.S. PATENT DOCUMENTS 4,494,539 A   1/1985  Zenitani
4,641,649 A   2/1987  Walinsky
(Continued)

FOREIGN PATENT DOCUMENTS

GB    2388039    11/2003
GB    2406521    4/2005
(Continued)

OTHER PUBLICATIONS

International Search Report and Written Opinion; International Patent Application No. PCT/IB2019/060784; dated Oct. 3, 2020; 6 pages.

*Primary Examiner* — Thomas A Giuliani
(74) *Attorney, Agent, or Firm* — CASIMIR JONES, SC; Robert A. Goetz

(57) ABSTRACT

The present invention relates to comprehensive systems, devices and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, systems, devices, and methods are provided for treating a tissue region (e.g., a tumor) through application of energy using energy delivery devices having a conductive permanent tip encapsulated in a biocompatible material.

16 Claims, 2 Drawing Sheets

(52) U.S. Cl.
CPC .............. *A61B 2018/00982* (2013.01); *A61B 2018/1838* (2013.01); *A61B 2018/1869* (2013.01)

(58) Field of Classification Search
USPC .............. 606/33, 41; 607/99, 101, 103, 116, 607/154–156
See application file for complete search history.

(56) References Cited

U.S. PATENT DOCUMENTS

| | | | |
|---|---|---|---|
| 5,246,438 A | 9/1993 | Langberg | |
| 5,314,466 A | 5/1994 | Stern | |
| 5,358,515 A | 10/1994 | Hurter | |
| 5,364,392 A | 11/1994 | Warner | |
| 5,405,346 A | 4/1995 | Grundy | |
| 5,603,697 A | 2/1997 | Grundy | |
| 5,658,326 A | 8/1997 | Barsne | |
| 5,693,082 A | 12/1997 | Warner | |
| 5,697,949 A | 12/1997 | Giurtino | |
| 5,741,249 A | 4/1998 | Moss | |
| 5,788,692 A | 8/1998 | Campbell | |
| 5,800,494 A | 9/1998 | Campbell | |
| 5,810,803 A | 9/1998 | Moss | |
| 5,957,969 A | 9/1999 | Warner | |
| 6,016,811 A | 1/2000 | Knopp | |
| 6,026,331 A | 2/2000 | Feldberg | |
| 6,245,062 B1 | 6/2001 | Berube | |
| 6,251,128 B1 | 6/2001 | Knopp | |
| 6,277,113 B1 | 8/2001 | Berube | |
| 6,287,302 B1 | 9/2001 | Berube | |
| 6,306,132 B1 | 10/2001 | Moorman | |
| 6,312,427 B1 | 11/2001 | Berube | |
| 6,355,033 B1 | 3/2002 | Moorman | |
| 6,364,876 B1 | 4/2002 | Erb | |
| 6,383,182 B1 | 5/2002 | Berube | |
| 6,461,351 B1 | 10/2002 | Woodruff | |
| 6,471,696 B1 | 10/2002 | Berube | |
| 6,527,768 B2 | 3/2003 | Berube | |
| 6,577,903 B1 | 6/2003 | Cronin | |
| 6,582,486 B1 | 6/2003 | Delpiano | |
| 6,635,055 B1 | 10/2003 | Cronin | |
| 6,652,520 B2 | 11/2003 | Moorman | |
| 6,817,976 B2 | 11/2004 | Rovegno | |
| 6,817,999 B2 | 11/2004 | Berube | |
| 6,823,218 B2 | 11/2004 | Berube | |
| 6,878,147 B2 | 4/2005 | Prakash | |
| 6,893,436 B2 | 5/2005 | Woodard | |
| 6,962,586 B2 | 11/2005 | Berube | |
| 6,972,016 B2 | 12/2005 | Hill | |
| 7,033,352 B1 | 4/2006 | Gauthier | |
| 7,101,369 B2 | 9/2006 | van der Weide | |
| 7,147,632 B2 | 12/2006 | Prakash | |
| 7,244,254 B2 | 7/2007 | Brace | |
| 7,318,824 B2 | 1/2008 | Prakash | |
| 7,331,960 B2 | 2/2008 | Schaer | |
| 7,467,015 B2 | 12/2008 | van der Weide | |
| 7,875,024 B2 | 1/2011 | Turovskiy | |
| 8,672,932 B2 | 3/2014 | van der Weide | |
| 9,192,438 B2 | 11/2015 | Thiel | |
| 10,363,092 B2 | 7/2019 | van der Weide | |
| 2003/0093007 A1 | 5/2003 | Wood | |
| 2005/0075629 A1 | 4/2005 | Chapelon | |
| 2006/0004351 A1* | 1/2006 | Arless | A61B 18/02 606/41 |
| 2006/0276781 A1 | 12/2006 | van der Weide | |
| 2006/0293652 A1 | 12/2006 | van der Weide | |
| 2007/0016180 A1 | 1/2007 | Lee | |
| 2007/0016181 A1 | 1/2007 | van der Weide | |
| 2007/0055224 A1 | 3/2007 | Lee | |
| 2007/0288079 A1 | 12/2007 | van der Weide | |
| 2008/0045938 A1 | 2/2008 | van der Weide | |
| 2011/0009728 A1 | 1/2011 | Schouenborg | |
| 2013/0190851 A1 | 7/2013 | Schouenborg | |
| 2014/0046175 A1* | 2/2014 | Ladtkow | A61B 5/01 606/33 |
| 2015/0289788 A1 | 10/2015 | Simpson | |
| 2015/0320481 A1* | 11/2015 | Cosman, Jr. | A61B 34/10 606/35 |
| 2019/0247117 A1 | 8/2019 | Schaning | |

FOREIGN PATENT DOCUMENTS

| | | |
|---|---|---|
| WO | WO 1995/004385 | 2/1995 |
| WO | WO 2003/039385 | 5/2003 |
| WO | WO 2003/053259 | 7/2003 |
| WO | WO 2003/088858 | 10/2003 |
| WO | WO 2004/026122 | 4/2004 |
| WO | WO 2004/033039 | 4/2004 |
| WO | WO 2004/112628 | 12/2004 |
| WO | WO 2005/034783 | 4/2005 |
| WO | WO 2006/002943 | 1/2006 |
| WO | WO 2006/004585 | 1/2006 |
| WO | WO 2006/005579 | 1/2006 |
| WO | WO 2006/008481 | 1/2006 |
| WO | WO 2008/091197 | 7/2008 |
| WO | WO 2018/222101 | 12/2018 |

* cited by examiner

ENERGY DELIVERY DEVICES AND RELATED SYSTEMS AND METHODS THEREOF

CROSS-REFERENCE TO RELATED APPLICATION

The present invention claims the priority benefit of U.S. Provisional Patent Application 62/779,299, filed Dec. 13, 2018, which is hereby incorporated by reference.

FIELD OF THE INVENTION

The present invention relates to comprehensive systems, devices and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, systems, devices, and methods are provided for treating a tissue region (e.g., a tumor) through application of energy using energy delivery devices having a permanent sharp tip encapsulated in a biocompatible material.

BACKGROUND

Ablation is an important therapeutic strategy for treating certain tissues such as benign and malignant tumors, cardiac arrhythmias, cardiac dysrhythmias and tachycardia. Most approved ablation systems utilize radio frequency (RF) energy as the ablating energy source. Accordingly, a variety of RF based catheters and power supplies are currently available to physicians. However, RF energy has several limitations, including the rapid dissipation of energy in surface tissues resulting in shallow "burns" and failure to access deeper tumor or arrhythmic tissues. Another limitation of RF ablation systems is the tendency of eschar and clot formation to form on the energy emitting electrodes which limits the further deposition of electrical energy.

Microwave energy is an effective energy source for heating biological tissues and is used in such applications as, for example, cancer treatment and preheating of blood prior to infusions. Accordingly, in view of the drawbacks of the traditional ablation techniques, there has recently been a great deal of interest in using microwave energy as an ablation energy source. The advantage of microwave energy over RF is the deeper penetration into tissue, insensitivity to charring, lack of necessity for grounding, more reliable energy deposition, faster tissue heating, and the capability to produce much larger thermal lesions than RF, which greatly simplifies the actual ablation procedures. Accordingly, there are a number of devices under development that utilize electromagnetic energy in the microwave frequency range as the ablation energy source (see, e.g., U.S. Pat. Nos. 4,641,649, 5,246,438, 5,405,346, 5,314,466, 5,800,494, 5,957,969, 6,471,696, 6,878,147, and 6,962,586; each of which is herein incorporated by reference in their entireties).

Unfortunately, current devices configured to deliver microwave energy have drawbacks. For example, the tips of energy delivery devices are designed to be sharp enough to penetrate tissue and lesions or even pierce through an airway wall if required. However such sharp tips can lead to difficulties in navigating through tight curves and turns when placed through an endoscopic sheath or extended working channel (EWC). The tip can sometimes catch on the PTFE liner, metallic braiding, or embedded marker band which can cause damage of the sheath, either scrapping the liner and increasing the force to insert the probe or, in extreme cases, piercing through the side wall of the sheath. This could lead to unintended airway lacerations, scrapes, punctures, or other patient harm. This risk is currently mitigated by offering multiple flexible probe tip variants that a user can select depending on the target location. Locations that are more apical or requiring navigation through tight turns may require use of a duller or shorter tip. That reduces the risk of catching on the sheath. However, once the shorter probe tip reaches the target location, it may be more difficult to penetrate a target tissue/lesion.

As such, improved energy delivery devices having permanent sharp tips capable of placement through an endoscopic sheath without risk for damaging such an endoscopic sheath are needed.

The present invention addresses this need.

SUMMARY OF THE INVENTION

The present invention relates to comprehensive systems, devices and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, systems, devices, and methods are provided for treating a tissue region (e.g., a tumor) through application of energy using energy delivery devices having a permanent sharp tip encapsulated in a biocompatible material.

In some embodiments, the present invention provides energy delivery device comprising an antenna comprising an inner conductor; and a permanent sharp tip positioned at the distal end of the antenna, wherein the permanent sharp tip is encapsulated in a biocompatible material thereby rendering the distal end of the energy delivery device non-sharp.

Such energy delivery devices are not limited to a particular shape or size dimensions for the biocompatible material encapsulating the permanent sharp tip. In some embodiments, the width of the biocompatible material is not larger than the width of the antenna. In some embodiments, the biocompatible material is bullet shaped. In some embodiments, the biocompatible material is dome shaped. In some embodiments, the biocompatible material is cylindrically shaped. In some embodiments, the shape of the biocompatible material is consistent with the shape of the antenna.

Such energy delivery devices are not limited to a particular material for the biocompatible material encapsulating the permanent sharp tip. In some embodiments, the biocompatible material is any material that upon exposure to ablation energy will disintegrate and/or melt and/or dissolve and/or sublime. In some embodiments, the biocompatible material is any material that upon exposure to ablation energy will disintegrate and/or melt and/or dissolve and/or sublime resulting in a non-encapsulated conductive permanent sharp tip. In some embodiments, the biocompatible material is ice or wax. In some embodiments, the biocompatible material is a low-melt temperature plastic. In some embodiments, the biocompatible material is a food-like substance (e.g., gelatin) (e.g., candied sugar). In some embodiments, the biocompatible material is carbon dioxide (e.g., dry ice).

Such energy delivery devices are not limited to a particular type or kind of permanent sharp tip. In some embodiments, the permanent sharp tip is a conductive permanent sharp tip. In some embodiments, the permanent sharp tip is a non-conductive permanent sharp tip.

Such energy delivery devices are not limited to a particular material or shape for the permanent sharp tip. In some embodiments, the permanent sharp tip is cone shaped. In some embodiments, the permanent sharp tip is titanium based. In some embodiments, the permanent sharp tip is coated with a non-stick material. In some embodiments, the permanent sharp tip is fluoropolymer based. In some embodiments, the permanent sharp tip is a beveled needle. In some embodiments, the permanent sharp tip is trifaceted. In some embodiments, the permanent sharp tip is ceramic based. In some embodiments, the permanent sharp tip is high temperature plastic based. In some embodiments, the permanent sharp tip has a diamond like coating. In some embodiments, the diamond like coating is a dielectric material. In some embodiments, the diamond like coating is less than 20 microns. In some embodiments, the permanent sharp tip has a plurality of micro-serrations. In some embodiments, the micro-serrations are in a tri-facet or quad-facet design. In some embodiments, the micro-serrations are 50-100 μm in length. In some embodiments, the permanent sharp tip features a plurality of scales adjacent to the micro-serrations. In some embodiments, the permanent sharp tip comprises a trocar.

Such embodiments are not limited to particular aspects for the antenna having an inner conductor. In some embodiments, the inner conductor is not physically coupled to the permanent sharp tip (e.g., conductive permanent sharp tip). In some embodiments, the inner conductor is capacitively-coupled to the permanent sharp tip.

In some embodiments, the antenna comprises a conductive outer conductor surrounding at least a portion of the inner conductor. In some embodiments, the antenna comprises a dielectric material between the inner and outer conductors. In some embodiments, the antenna is a triaxial antenna. In some embodiments, the inner conductor comprises a first region distal to a second region, the second region distal to a third region, wherein the third region is contained in a triaxial antenna, wherein the second region lacks an outer conductor of the triaxial antenna, and wherein the first region lacks an outer conductor and dielectric material of the triaxial antenna. In some embodiments, the first region is adhered to and surrounded by a metal fitting. In some embodiments, the metal fitting is a brass metal fitting. In some embodiments, the metal fitting extends distally beyond the most distal end of the inner conductor. In some embodiments, the metal filling abuts a dielectric material surrounding the inner conductor in the second region. In some embodiments, the second region comprises a proximal portion containing dielectric material of the triaxial antenna and a distal portion lacking the dielectric material of the triaxial antenna. In some embodiments, the distal portion of the second region comprises a non-conductive sleeve surrounding the inner conductor. In some embodiments, the non-conductive sleeve comprises PTFE. In some embodiments, the permanent sharp tip is attached to an insulator, the insulator attached to a distal end of the metal fitting. In some embodiments, the insulator comprises a ceramic insulator. In some embodiments, the metal fitting, insulator, and conductive tip are positioned and dimensioned so as to generate a low impedance overlap to transfer energy to the conductive tip when energy is supplied to the inner conductor. In some embodiments, the metal fitting is adhered to the inner conductor via an electrically conductive adhesive.

In certain embodiments, the present invention provides systems comprising such energy delivery devices and a power supply electrically connected to the device. In some embodiments, the power supply generates microwave energy. In some embodiments, the systems further comprise a coolant supply in fluid communication with the device. In some embodiments, the coolant supply comprises carbon dioxide. In some embodiments, the antenna has a plug that prevents coolant from flowing to the distal end of the antenna. In some embodiments, the systems further comprise a control processor that regulates energy deliver from the power supply to the antenna and coolant delivery to the antenna.

In certain embodiments, the present invention provides methods of ablating a tissue region, comprising guiding such an energy delivery device through a sheath to a target tissue location, wherein the energy delivery device does not pierce the sheath through the guiding, providing energy to the energy delivery device, wherein the biocompatible material disintegrates upon exposure to the energy from the energy delivery device thereby exposing the permanent sharp tip to the target tissue location; and providing ablation energy to the target tissue location. In some embodiments, the tissue region comprises a tumor. In some embodiments, the tissue region is within a living subject. In some embodiments, the tissue region is within a living human subject.

Additional embodiments are described herein.

DETAILED DESCRIPTION

Figure 1:
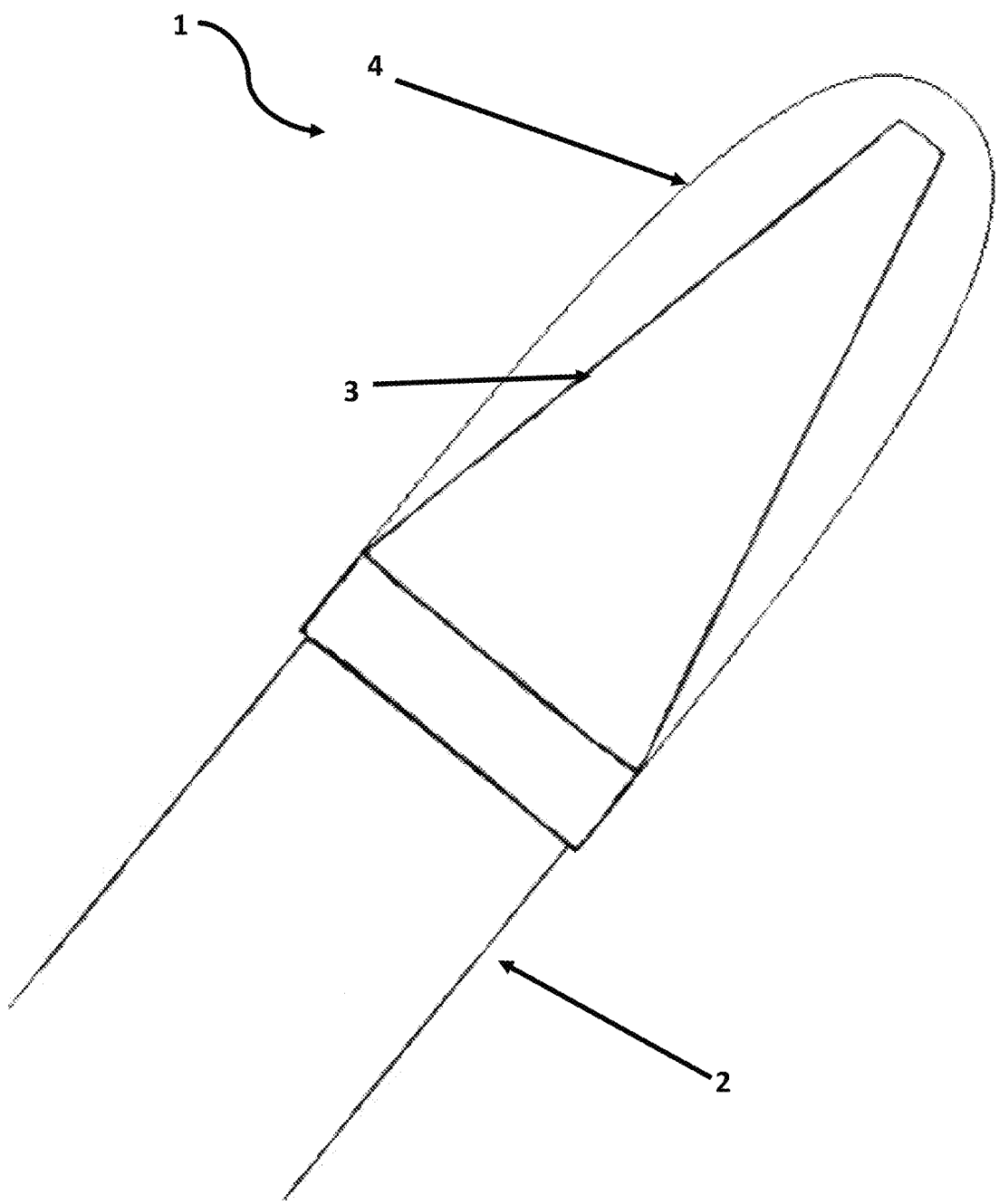
FIG. 1 shows exemplary energy delivery device having an antenna and a permanent sharp tip encapsulated with a biocompatible encapsulation.

Insertion into a tissue region with current energy delivery devices requires a high insertion force that can result in undesired effects. For example, such high insertion forces can tear a tissue region, and/or deflect the device to an undesired position (e.g., misplacement of the device). As such, energy delivery devices having f tips are required. However, such energy delivery devices have drawbacks. Indeed, such devices having sharp tips can lead to difficulties in navigating through tight curves and turns when placed through an endoscopic sheath or extended working channel (EWC). The tip can sometimes catch on the PTFE liner, metallic braiding, or embedded marker band which can cause damage of the sheath, either scrapping the liner and increasing the force to insert the probe or, in extreme cases, piercing through the side wall of the sheath. This could lead to unintended airway lacerations, scrapes, punctures, or other patient harm. This risk is currently mitigated by offering multiple flexible probe tip variants that a user can select depending on the target location. Locations that are more apical or requiring navigation through tight turns may require use of a duller or shorter tip. That reduces the risk of catching on the sheath. However, once the shorter probe tip reaches the target location, it may be more difficult to penetrate a target tissue/lesion.

The present invention addresses this limitation through providing improved energy delivery devices having permanent sharp tips capable of placement through an endoscopic sheath without risk for damaging such an endoscopic sheath.

Accordingly, provided herein are energy delivery devices (e.g., for use in ablation procedures) comprising an antenna and a permanent sharp tip (e.g., a conductive permanent sharp tip) positioned at the distal end of the antenna, wherein the tip is encapsulated in a biocompatible material thereby rendering the distal end of the devices as non-sharp. In some embodiments, such energy delivery devices enable a user to place a device through a endoscopic sheath without risk for damaging (e.g., catching, piercing) the sheath. In some embodiments, such devices are integrated into systems described herein and in US. Pat. No. 9,192,438.

The present invention relates to comprehensive systems, devices and methods for delivering energy (e.g., microwave energy, radiofrequency energy) to tissue for a wide variety of applications, including medical procedures (e.g., tissue ablation, resection, cautery, vascular thrombosis, intraluminal ablation of a hollow viscus, cardiac ablation for treatment of arrhythmias, electrosurgery, tissue harvest, cosmetic surgery, intraocular use, etc.). In particular, the present invention provides systems for the delivery of energy (e.g., microwave energy) comprising a power supply, a means of directing, controlling and delivering power (e.g., a power splitter), a processor, an energy emitting device, a cooling system, an imaging system, a temperature monitoring system, and/or a tracking system. In certain embodiments, systems, devices, and methods are provided for treating a tissue region (e.g., a tumor) through use of the energy delivery systems of the present invention. In certain embodiments, systems, devices, and methods are provided for treating a tissue region (e.g., a tumor) through application of energy using ablation tools comprising an antenna and a permanent sharp tip positioned at the distal end of the antenna, wherein the permanent sharp tip is encapsulated in a biocompatible material thereby rendering the distal end of the devices as non-sharp.

The systems of the present invention may be combined within various system/kit embodiments. For example, the present invention provides systems comprising one or more of a generator, a power distribution system, a means of directing, controlling and delivering power (e.g., a power splitter), an energy applicator, along with any one or more accessory component (e.g., surgical instruments, software for assisting in procedure, processors, temperature monitoring devices, etc.). The present invention is not limited to any particular accessory component.

The systems of the present invention may be used in any medical procedure (e.g., percutaneous or surgical) involving delivery of energy (e.g., radiofrequency energy, microwave energy, laser, focused ultrasound, etc.) to a tissue region. The systems are not limited to treating a particular type or kind of tissue region (e.g., brain, liver, heart, blood vessels, foot, lung, bone, etc.). For example, the systems of the present invention find use in ablating tumor regions. Additional treatments include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, primary or metastatic tumors. In some embodiments, the surgical application comprises the control of hemorrhage (e.g. electrocautery). In some embodiments, the surgical application comprises tissue cutting or removal. In some embodiments, the device is configured for movement and positioning, with minimal damage to the tissue or organism, at any desired location, including but not limited to, the brain, neck, chest, abdomen, pelvis, and extremities. In some embodiments, the device is configured for guided delivery, for example, by computerized tomography, ultrasound, magnetic resonance imaging, fluoroscopy, and the like.

The illustrated embodiments provided below describe the systems and energy delivery devices having an antenna and a permanent sharp tip (e.g., a conductive permanent sharp tip) positioned at the distal end of the antenna, wherein the permanent sharp tip is encapsulated in a biocompatible material thereby rendering the distal end of the devices as non-sharp in terms of medical applications (e.g., ablation of tissue through delivery of microwave energy). However, it should be appreciated that such systems and devices of the present invention are not limited to medical applications. Such devices and systems may be used in any setting requiring delivery of energy to a load (e.g., agricultural settings, manufacture settings, research settings, etc.). The illustrated embodiments describe the devices and systems of the present invention in terms of microwave energy. It should be appreciated that the devices and systems of the present invention are not limited to a particular type of energy (e.g., radiofrequency energy, microwave energy, focused ultrasound energy, laser, plasma). As used herein, the terms "energy delivery device", "energy delivery device having an antenna", and "energy delivery devices having an antenna and a permanent sharp tip positioned at the distal end of the antenna, wherein the permanent sharp tip is encapsulated in a biocompatible material thereby rendering the distal end of the devices as non-sharp" are used interchangeably.

Systems of the present invention are not limited to any particular component or number of components. In some embodiments, the systems of the present invention include, but are not limited to including, a power supply, a means of directing, controlling and delivering power (e.g., a power splitter), a processor, an energy delivery device as described herein, a cooling system, an imaging system, and/or a tracking system. When multiple antennas are in use, the system may be used to individually control each antenna separately.

In some embodiments, energy delivery devices having an antenna and permanent sharp tip (e.g., a conductive permanent sharp tip) positioned at the distal end of the antenna, wherein the permanent sharp tip is encapsulated in a biocompatible material thereby rendering the distal end of the devices as non-sharp are provided as part of an energy delivery system comprising a device described herein, a power supply, a transmission line, a power distribution component (e.g., power splitter), a processor, an imaging system, and a temperature monitoring system. In some embodiments, the components of the energy delivery systems are connected via a transmission line, cables, etc. In some embodiments, the energy delivery is separated from the power supply, a means of directing, controlling and delivering power (e.g., a power splitter), processor, imaging system, temperature monitoring system across a sterile field barrier.

In some embodiments, the energy delivery devices have a tip with improved sharpness and penetrability. Such devices exhibit reduced insertion forces and improved ease of use.

In certain embodiments, the present invention provides an energy delivery device comprising an antenna comprising an inner conductor; and a permanent sharp tip positioned at the distal end of the antenna, wherein the conductive tip is encapsulated in a biocompatible material thereby rendering the distal end of the energy delivery device non-sharp.

FIG. 1 shows an energy delivery device 1 having an antenna 2 and a permanent sharp tip 3 positioned at the distal end of the antenna 2, wherein the permanent sharp tip 3 is encapsulated with a biocompatible encapsulation 4.

Still referring to FIG. 1, the biocompatible encapsulation 4 is not limited to a particular shape or size dimensions. In some embodiments, the shape and size dimensions of the biocompatible encapsulation 4 are such that each does not hinder the placement of the energy delivery device 1 through a sheath (e.g., endoscopic sheath).

In some embodiments, as shown in FIG. 1, the shape of the biocompatible encapsulation 4 is bullet shaped. In some embodiments, the shape of the biocompatible encapsulation 4 is dome shaped. In some embodiments, the shape of the biocompatible encapsulation 4 is cylindrical. In some embodiments, the shape of the biocompatible encapsulation 4 is such that it does not hinder the placement of the energy delivery device 1 through a sheath (e.g., endoscopic sheath).

In some embodiments, the length of the biocompatible encapsulation 4 is such that it is able to render the distal end of the energy delivery device 1 non-sharp. In some embodiments, the length of the biocompatible encapsulation 4 is such that it encapsulates at least the sharp portion of the permanent sharp tip 3 (e.g., 1%, 2%, 3.5%, 10%, 15%, 20%, 23%, 25%, 28%, 33%, 40%, 50%, 65%, 70%, 80%, 82%, 83%, 88%, 90%, 95%, 98%, 99%, 99.9999% of the conductive permanent sharp tip 3). In some embodiments, the length of the biocompatible encapsulation 4 is such that it encapsulates the entire permanent sharp tip 3. In some embodiments, the length of the biocompatible encapsulation 4 is such that it does not hinder the placement of the energy delivery device 1 through a sheath (e.g., endoscopic sheath).

In some embodiments, the width of the biocompatible encapsulation 4 is equal to or less than the width of the antenna 2. In some embodiments, the width of the biocompatible encapsulation 4 is such that it does not hinder the placement of the energy delivery device 1 through a sheath (e.g., endoscopic sheath).

Still referring to FIG. 1, such energy delivery devices 1 are not limited to a particular composition for the biocompatible encapsulation 4. In some embodiments, the composition of the biocompatible encapsulation 4 is such that it is able to encapsulate the permanent sharp tip 3 in a manner such that the energy delivery device 1 is able to be placed through a sheath (e.g., an endoscopic sheath) without catching or piercing the sheath. In some embodiments, the composition of the biocompatible encapsulation 4 is such that it is able to encapsulate the permanent sharp tip 3 in a manner such that the energy delivery device 1 is able to remove (e.g., disintegrate and/or melt and/or dissolve and/or sublime) the biocompatible encapsulation 4 upon contact with a tissue region. In some embodiments, the composition of the biocompatible encapsulation 4 is such that it is able to encapsulate the permanent sharp tip 3 in a manner such that the energy delivery device 1 is able to remove (e.g., disintegrate and/or melt and/or dissolve and/or sublime) the biocompatible encapsulation 4 upon exposure to ablation energy thereby exposing the permanent sharp tip 3.

In some embodiments, the composition of the biocompatible encapsulation 4 is a biocompatible material. Such embodiments are not limited to a particular biocompatible material.

In some embodiments, the biocompatible material is ice. For example, in some embodiments, the permanent sharp tip 3 is encapsulated in an ice-based biocompatible encapsulation 4.

Such embodiments are not limited to a particular manner of encapsulating the permanent sharp tip 3 in an ice-based biocompatible encapsulation 4. In some embodiments, water (e.g., sterile water) is frozen over a portion (e.g., 1%, 2%, 3.5%, 10%, 15%, 20%, 23%, 25%, 28%, 33%, 40%, 50%, 65%, 70%, 80%, 82%, 83%, 88%, 90%, 95%, 98%, 99%, 99.9999%) of the permanent sharp tip 3 at least including the sharp tip thereby yielding a biocompatible encapsulation 4. In some embodiments, water is frozen over the entirety of the permanent sharp tip 3 thereby yielding a biocompatible encapsulation 4. In some embodiments, a mold (e.g., plastic mold, ceramic mold, cast-iron mold, silicon mold, etc.) is used to ensure any desired shape (e.g., bullet shaped, cylindrical, dome) for the biocompatible encapsulation 4.

In some embodiments, an external freezing temperature is applied to water and the conductive permanent sharp tip 3 for purposes of rendering an ice-based biocompatible encapsulation 4. In such embodiments, the ice-based biocompatible encapsulation 4 naturally melts over a period of time or upon exposure to a non-freezing temperature.

In some embodiments, a freezing temperature through the energy delivery device is applied to water and the permanent sharp tip 3 for purposes of rendering an ice-based biocompatible encapsulation 4. In some embodiments, carbon dioxide gas is supplied to the water and the permanent sharp tip 3 through the antenna 2 of the energy delivery device 1. In such embodiments, the freezing temperature supplied through the energy delivery device 1 can be maintained until it is desired that the biocompatible encapsulation 4 dissolves.

In some embodiments, the biocompatible material is wax. For example, in some embodiments, the permanent sharp tip 3 is encapsulated in a wax-based biocompatible encapsulation 4. Such embodiments are not limited to a particular type or kind of wax.

Still referring to FIG. 1, such embodiments are not limited to a particular manner of encapsulating the permanent sharp tip 3 in a wax-based biocompatible encapsulation 4. In some embodiments, wax is adhered over a portion (e.g., 1%, 2%, 3.5%, 10%, 15%, 20%, 23%, 25%, 28%, 33%, 40%, 50%, 65%, 70%, 80%, 82%, 83%, 88%, 90%, 95%, 98%, 99%, 99.9999%) of the permanent sharp tip 3 at least including the sharp tip thereby yielding a biocompatible encapsulation 4. In some embodiments, wax is adhered over the entirety of the permanent sharp tip 3 thereby yielding a biocompatible encapsulation 4. In some embodiments, a mold (e.g., plastic mold, ceramic mold, cast-iron mold, etc.) is used to ensure a desired shape (e.g., bullet shaped, cylindrical, dome) for the biocompatible encapsulation 4. In such embodiments, the wax-based biocompatible encapsulation 4 naturally melts upon exposure to over a period of time or upon exposure to a temperature higher than normal body temperature. In such embodiments, the wax-based biocompatible encapsulation 4 naturally melts upon exposure to over a period of time or upon exposure to a temperature higher than normal body temperature but low enough that it does not cause tissue damage (e.g., approximately 45C).

In some embodiments, the biocompatible material is low melt temperature plastic. For example, in some embodiments, the permanent sharp tip 3 is encapsulated in a low melt temperature plastic-based biocompatible encapsulation 4. Such embodiments are not limited to a particular type or kind of low melt temperature plastic.

Still referring to FIG. 1, such embodiments are not limited to a particular manner of encapsulating the permanent sharp tip 3 in a low melt temperature plastic-based biocompatible encapsulation 4. In some embodiments, low melt temperature plastic is adhered over a portion (e.g., 1%, 2%, 3.5%, 10%, 15%, 20%, 23%, 25%, 28%, 33%, 40%, 50%, 65%, 70%, 80%, 82%, 83%, 88%, 90%, 95%, 98%, 99%, 99.9999%) of the permanent sharp tip 3 at least including the sharp tip thereby yielding a biocompatible encapsulation 4. In some embodiments, low melt temperature plastic is adhered over the entirety of the permanent sharp tip 3 thereby yielding a biocompatible encapsulation 4. In some embodiments, a mold (e.g., plastic mold, ceramic mold, cast-iron mold, etc.) is used to ensure a desired shape (e.g., bullet shaped, cylindrical, dome) for the biocompatible encapsulation 4. In such embodiments, the low melt temperature plastic-based biocompatible encapsulation 4 naturally melts upon exposure to over a period of time or upon exposure to a temperature higher than normal body temperature. In such embodiments, the low melt temperature plastic-based biocompatible encapsulation 4 naturally melts upon exposure to over a period of time or upon exposure to a temperature higher than normal body temperature but low enough that it does not cause tissue damage (e.g., approximately 45 C).

In some embodiments, the biocompatible material is a food-like substance. For example, in some embodiments, the permanent sharp tip 3 is encapsulated in a food-like substance-based biocompatible encapsulation 4. Such embodiments are not limited to a particular type or kind of food-like substance. In some embodiments, the food-like substance is gelatin based. In some embodiments, the food-like substance is candied sugar based. Still referring to FIG. 1, such embodiments are not limited to a particular manner of encapsulating the permanent sharp tip 3 in a food-like substance-based biocompatible encapsulation 4. In some embodiments, food-like substance is adhered over a portion (e.g., 1%, 2%, 3.5%, 10%, 15%, 20%, 23%, 25%, 28%, 33%, 40%, 50%, 65%, 70%, 80%, 82%, 83%, 88%, 90%, 95%, 98%, 99%, 99.9999%) of the permanent sharp tip 3 at least including the sharp tip thereby yielding a biocompatible encapsulation 4. In some embodiments, food-like substance is adhered over the entirety of the permanent sharp tip 3 thereby yielding a biocompatible encapsulation 4. In some embodiments, a mold (e.g., plastic mold, ceramic mold, cast-iron mold, etc.) is used to ensure a desired shape (e.g., bullet shaped, cylindrical, dome) for the biocompatible encapsulation 4. In such embodiments, the food-like substance-based biocompatible encapsulation 4 naturally dissolves / melts upon exposure to over a period of time or upon exposure to a temperature higher than normal body temperature. In such embodiments, the food-like substance-based biocompatible encapsulation 4 naturally dissolves / melts upon exposure to over a period of time or upon exposure to a temperature higher than normal body temperature but low enough that it does not cause tissue damage (e.g., approximately 45C).

In some embodiments, the biocompatible material is carbon dioxide (e.g., dry ice). For example, in some embodiments, the permanent sharp tip 3 is encapsulated in a dry ice-based biocompatible encapsulation 4.

Such embodiments are not limited to a particular manner of encapsulating the permanent sharp tip 3 in a dry ice-based biocompatible encapsulation 4. In some embodiments, carbon dioxide is frozen over a portion (e.g., 1%, 2%, 3.5%, 10%, 15%, 20%, 23%, 25%, 28%, 33%, 40%, 50%, 65%, 70%, 80%, 82%, 83%, 88%, 90%, 95%, 98%, 99%, 99.9999%) of the permanent sharp tip 3 at least including the sharp tip thereby yielding a biocompatible encapsulation 4. In some embodiments, carbon dioxide is frozen over the entirety of the permanent sharp tip 3 thereby yielding a biocompatible encapsulation 4. In some embodiments, a mold (e.g., plastic mold, ceramic mold, cast-iron mold, silicon mold, etc.) is used to ensure any desired shape (e.g., bullet shaped, cylindrical, dome) for the biocompatible encapsulation 4.

In some embodiments, an external freezing temperature is applied to the dry ice and the conductive permanent sharp tip 3 for purposes of rendering a dry ice-based biocompatible encapsulation 4. In such embodiments, the dry ice-based biocompatible encapsulation 4 naturally sublimes over a period of time or upon exposure to a non-freezing temperature.

In some embodiments, the surface of the permanent sharp tip 3 has thereon one or more structural features for facilitating encapsulation of the permanent sharp tip 3 with the biocompatible material. For example, in some embodiments, the permanent sharp tip 3 has thereon a surface geometry that facilitates the biocompatible material to flow into such surface geometry thereby providing a base from which the biocompatible material can encapsulate the permanent sharp tip 3. In some embodiments, the surface geometry facilitates a flowing of the biocompatible material around such features and thereby locking the biocompatible material onto the permanent sharp tip 3 (resulting in a mechanical hold and an adhesive hold of the encapsulation).

Such devices are not limited to a particular type or kind of structural feature on the surface of the permanent sharp tip 3 for facilitating encapsulation of the permanent sharp tip 3 with the biocompatible material. In some embodiments, the surface of the permanent sharp tip 3 has thereon a surface roughening (e.g., peaks and valleys on the surface from which the biocompatible material can flow into). In some embodiments, the permanent sharp tip 3 has thereon a knurled surface. In some embodiments, the surface of the permanent sharp tip 3 has thereon an annular groove or undercut ring. In some embodiments, the surface of the permanent sharp tip 3 has thereon an annular protrusion. In some embodiments, the surface of the permanent sharp tip 3 has angled ribs and/or undercuts facilitating a flowing of the biocompatible material around such features and thereby locking them onto the permanent sharp tip 3.

Figure 2:
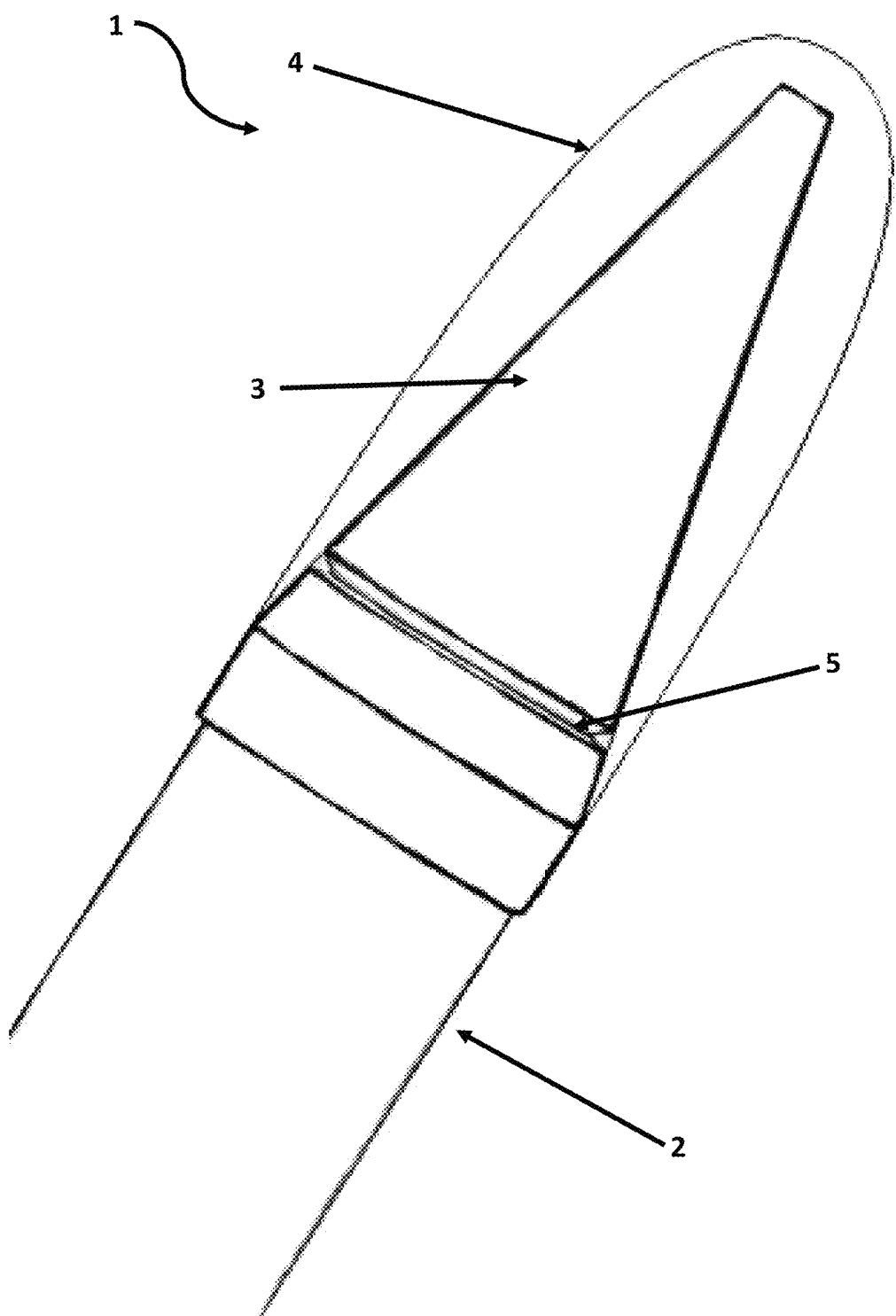
FIG. 2 shows exemplary energy delivery device having an antenna and a permanent sharp tip encapsulated with a biocompatible encapsulation, and an annular groove or undercut ring as a structural feature on the surface of the permanent sharp tip for facilitating encapsulation of the permanent sharp tip with the biocompatible material

FIG. 2 shows a permanent sharp tip having an annular groove or undercut ring as a structural feature 5 on the surface of the permanent sharp tip 3 for facilitating encapsulation of the permanent sharp tip 3 with the biocompatible material.

In some embodiments wherein carbon dioxide is not used as the biocompatible agent, carbon dioxide is used to encapsulate an encapsulated permanent sharp tip 3. In some embodiments, the carbon dioxide is applied following encapsulation of the permanent sharp tip 3 with the biocompatible material. In some embodiments, the biocompatible material and the carbon dioxide are simultaneously applied resulting in an encapsulation of the permanent sharp tip with the biocompatible material, and encapsulation of such encapsulation with the carbon dioxide. In some embodiments, the carbon dioxide adheres with the permanent sharp tip 3 through adherence with, onto or into the one or more structural features for facilitating encapsulation of the permanent sharp tip 3 with the biocompatible material. In some embodiments, the carbon dioxide adheres with the permanent sharp tip 3 through exposure to an encapsulated permanent sharp tip 3.

In some embodiments, a freezing temperature through the energy delivery device is applied to water and the permanent sharp tip 3 for purposes of rendering an ice-based biocompatible encapsulation 4. In some embodiments, carbon dioxide gas is supplied to the water and the permanent sharp tip 3 through the antenna 2 of the energy delivery device 1. In such embodiments, the freezing temperature supplied through the energy delivery device 1 can be maintained until it is desired that the biocompatible encapsulation 4 dissolves.

Still referring to FIG. 1, the energy delivery devices 1 are not limited to a particular type or kind of permanent sharp tip 3. In some embodiments, the permanent sharp tip 3 is any sharp tip capable of penetrating any desired tissue (e.g., tumor, bone, airway wall, muscle tissue, etc.) within a living organism (e.g., human, ape, pig, goat, dog, cat, etc.).

Such embodiments are not limited to a particular shape for the permanent sharp tip 3. In some embodiments, the shape of the permanent sharp tip 3 is such that it is able to penetrate any desired tissue (e.g., tumor, bone, airway wall, muscle tissue, etc.) within a living organism. In some embodiments, the shape of the permanent sharp tip 3 is such that it does not hinder the placement of the energy delivery device 1 through a sheath (e.g., endoscopic sheath). In some embodiments, the permanent sharp tip 3 is cone shaped. In some embodiments, the permanent sharp tip 3 is bullet shaped. In some embodiments, the permanent sharp tip 3 is cone shaped. In some embodiments, the permanent sharp tip 3 is needle shaped. In some embodiments, the permanent sharp tip 3 is cone shaped. In some embodiments, the permanent sharp tip 3 is trocar shaped.

Such embodiments are not limited to a particular type of permanent sharp tip 3. In some embodiments, the permanent sharp tip 3 is a conductive permanent sharp tip. In some embodiments, the permanent sharp tip 3 is a non-conductive permanent sharp tip.

In some embodiments, the conductive permanent tip 3 is a trocar. In some embodiments, the conductive permanent tip 3 is titanium based. In some embodiments, the conductive permanent tip 3 is non-stick material based (e.g., fluoropolymer). In some embodiments, the conductive permanent tip 3 is temperature-resistant material based (e.g., ceramic) (e.g., high temperature resistant plastic).

In some embodiments, the energy delivery devices 1 have a conductive permanent tip 3 with a diamond like coating (see, U.S. Provisional Patent Ser. No. 62/631,150). In some embodiments, the diamond like coating is a dielectric material. In some embodiments, the diamond like coating is less than 20 microns (e.g., less than 10 or less than 5 microns). In some embodiments, the tip is heat treated or subjected to electropolish pre-cleaning prior to coating. In some embodiments, the coating is applied via physical vapor deposition. In some embodiments, the coating is aluminum oxide or alumina. In some embodiments, the diamond like coating covers the entirety of the conductive permanent tip 3. In some embodiments, the diamond like coating covers the approximately the entirety (e.g., 65%, 70%, 75%, 78%, 79%, 80%, 85%, 88%, 90%, 91%, 92%, 95%, 97.5%, 98%, 99%, 99.5%, 99.999%) of the conductive permanent tip.

In some embodiments, the energy delivery devices 1 have a conductive permanent tip 3 with a plurality of micro-serrations (see, U.S. Provisional Patent Ser. No. 62/631,150). In some embodiments, the micro-serrations are in a tri-facet or quad-facet design. In some embodiments, the micro-serrations are 50-100 μm in length. In some embodiments, the device features a plurality of scales adjacent to the micro-serrations.

Such embodiments of the present invention contemplate the use of any type of antenna having an inner conductor for delivering (e.g., emitting) energy (e.g., ablation device, surgical device, etc.). Examples of applicable antennas include, but are not limited, to any of the antennas described in U.S. Pat. Nos. 7,101,369, 7,033,352, 6,893,436, 6,878,147, 6,823,218, 6,817,999, 6,635,055, 6,471,696, 6,383,182, 6,312,427, 6,287,302, 6,277,113, 6,251,128, 6,245,062, 6,026,331, 6,016,811, 5,810,803, 5,800,494, 5,788,692, 5,405,346, 4,494,539, U.S. patent application Ser. Nos. 11/728,460, 11/728,457, 11/728,428, 11/237,136, 11/236,985, 10/980,699, 10/961,994, 10/961,761, 10/834,802, 10/370,179, 09/847,181; U.S. Provisional Patent Ser. No. 62/631,150; Great Britain Patent Application Nos. 2,406,521, 2,388,039; European Patent No. 1395190; and International Patent Application Nos. WO 06/008481, WO 06/002943, WO 05/034783, WO 04/112628, WO 04/033039, WO 04/026122, WO 03/088858, WO 03/039385 WO 95/04385. Such antenna include any and all medical, veterinary, and research application devices configured for energy emission, as well as devices used in agricultural settings, manufacturing settings, mechanical settings, or any other application where energy is to be delivered.

As noted, the systems utilize energy delivery devices having therein antennae having inner conductors configured to emit energy (e.g., microwave energy, radiofrequency energy, radiation energy). The systems are not limited to particular types or designs of antennae (e.g., ablation device, surgical device, etc.). In some embodiments, the systems utilize energy delivery devices having linearly shaped antennae (see, e.g., U.S. Pat. Nos. 6,878,147, 4,494,539, U.S. patent application Ser. Nos. 11/728,460, 11/728,457, 11/728,428, 10/961,994, 10/961,761; and International Patent Application No., WO 03/039385). In some embodiments, the systems utilize energy delivery devices having non-linearly shaped antennae (see, e.g., U.S. Pat. Nos. 6,251,128, 6,016,811, and 5,800,494, U.S. patent application Ser. No. 9/847,181, and International Patent Application No. WO 03/088858). In some embodiments, the antennae have horn reflection components (see, e.g., U.S. Pat. Nos. 6,527,768, 6,287,302). In some embodiments, the antenna has a directional reflection shield (see, e.g., U.S. Pat. No. 6,312,427). In some embodiments, the antenna has therein a securing component so as to secure the energy delivery device within a particular tissue region (see, e.g., U.S. Pat. Nos. 6,364,876, and 5,741,249).

Generally, antennae configured to emit energy comprise coaxial transmission lines. The devices are not limited to particular configurations of coaxial transmission lines. Examples of coaxial transmission lines include, but are not limited to, coaxial transmission lines developed by Pasternack, Micro-coax, and SRC Cables. In some embodiments, the coaxial transmission line has a center conductor, a dielectric element, and an outer conductor (e.g., outer shield). In some embodiments, the antennae have flexible coaxial transmission lines (e.g., for purposes of positioning around, for example, pulmonary veins or through tubular structures) (see, e.g., U.S. Pat. Nos. 7,033,352, 6,893,436, 6,817,999, 6,251,128, 5,810,803, 5,800,494). In some embodiments, the antennae have rigid coaxial transmission lines (see, e.g., U.S. Pat. No. 6,878,1476, U.S. patent application Ser. Nos. 10/961,994, 10/961,761, and International Patent Application No. WO 03/039385).

In some embodiments, the energy delivery devices have a coaxial transmission line positioned within the antenna, and a coaxial transmission line connecting with the antenna. In some embodiments, the size of the coaxial transmission line within the antenna is larger than the coaxial transmission line connected with the antenna. The coaxial transmission line within the antenna and the coaxial transmission line connecting with the antenna are not limited to particular sizes. For example, in some embodiments, whereas the coaxial transmission line connected with the antenna is approximately 0.032 inches, the size of the coaxial transmission line within the antenna is larger than 0.032 inches (e.g., 0.05 inches, 0.075 inches, 0.1 inches, 0.5 inches). In some embodiments, the coaxial transmission line within the antenna has an inner conductor that is stiff and thick. In some embodiments, the end of the coaxial transmission line within the antenna is sharpened for percutaneous use. In some embodiments, the dielectric coating of the coaxial transmission line within the antenna is PTFE (e.g., for purposes of smoothing transitions from a cannula to an inner conductor (e.g., a thin and sharp inner conductor)).

Such embodiments are not limited to a particular coaxial transmission line shape. Indeed, in some embodiments, the shape of the coaxial transmission line and/or the dielectric element is selected and/or adjustable to fit a particular need.

In some embodiments, the outer conductor is a 20-gauge needle or a component of similar diameter to a 20-gauge needle. Preferably, for percutaneous use, the outer conductor is not larger than a 17-gauge needle (e.g., no larger than a 16-gauge needle). In some embodiments, the outer conductor is a 17-gauge needle. However, in some embodiments, larger devices are used, as desired. For example, in some embodiments, a 12-gauge diameter is used. The present invention is not limited by the size of the outer conductor. In some embodiments, the outer conductor is configured to fit within series of larger needles for purposes of assisting in medical procedures (e.g., assisting in tissue biopsy) (see, e.g., U.S. Pat. Nos. 6,652,520, 6,582,486, 6,355,033, 6,306,132). In some embodiments, the center conductor is configured to extend beyond the outer conductor for purposes of delivering energy to a desired location. In some embodiments, some or all of the feedline characteristic impedance is optimized for minimum power dissipation, irrespective of the type of antenna that terminates at its distal end.

In some embodiments, the energy delivery devices are provided with a proximal portion and a distal portion, wherein the distal portion is detachable and provided in a variety of different configurations that can attach to a core proximal portion. For example, in some embodiments, the proximal portion comprises a handle and an interface to other components of the system (e.g., power supply) and the distal portion comprises a detachable antenna having desired properties. A plurality of different antenna configured for different uses may be provided and attached to the handle unit for the appropriate indication.

In some embodiments, multiple (e.g., more than 1) (e.g., 2, 3, 4, 5, 10, 20, etc.) coaxial transmission lines and/or triaxial transmission lines are positioned within each energy delivery device for purposes of delivering high amounts of energy over an extended period of time.

In some embodiments, the energy delivery devices comprise a triaxial microwave probe with optimized tuning capabilities (see, e.g., U.S. Pat. No. 7,101,369; see, also, U.S. patent application Ser. Nos. 10/834,802, 11/236,985, 11/237,136, 11/237,430, 11/440,331, 11/452,637, 11/502, 783, 11/514,628; and International Patent Application No. PCT/US05/14534). The triaxial microwave probes are not limited to particular optimized tuning capabilities. In some embodiments, the triaxial microwave probes have pre-defined optimized tuning capabilities specific for a particular tissue type. In some embodiments, triaxial microwave probes are configured to ablate a smaller tissue region (e.g., ablating only the edge of an organ, ablating a small tumor, etc.). In such embodiments, the length of the first conductor is decreased (e.g., such that the wire contacts the tip of the so as to retain a small ablation region).

In some embodiments, the devices of the present invention are configured to attach with a detachable handle. The present invention is not limited to a particular type of detachable handle. In some embodiments, the detachable handle is configured to connect with multiple devices (e.g., 1, 2, 3, 4, 5, 10, 20, 50 . . . ) for purposes of controlling the energy delivery through such devices. In some embodiments, the handle is designed with a power amplifier for providing power to an energy delivery device.

In some embodiments, the energy delivery devices having an antenna with an inner conductor and a conductive permanent tip encapsulated in a biocompatible material are configured to have main bodies with both flexible and inflexible regions. The energy delivery devices are not limited to particular configurations for main bodies having both flexible and inflexible regions. In some embodiments, the flexible regions comprise plastic (e.g., PEEK). In some embodiments, the inflexible regions comprise ceramic. The flexible and inflexible regions are not limited to particular positions within the main bodies of the energy delivery devices. In some embodiments, the flexible region is positioned in a region experiencing lower amounts of microwave field emission. In some embodiments, the inflexible region is positioned in a region experiencing high amounts of microwave field emission (e.g., located over the proximal portion of the antenna to provide dielectric strength and mechanical rigidity). In some embodiments, the energy delivery devices have a heat shrink over the distal portion (e.g., the antenna) for providing additional durability. In some embodiments, as noted above, the energy delivery devices have a diamond like coating over the distal portion (e.g., the antenna) for providing additional sharpness.

In some embodiments, the material of the antenna is durable and provides a high dielectric constant. In some embodiments, the material of the antenna is zirconium and/or a functional equivalent of zirconium. In some embodiments, the energy delivery devices are provided as two or more separate antenna attached to the same or different power supplies. In some embodiments, the different antennas are attached to the same handle, while in other embodiments different handles are provided for each antenna. In some embodiments, multiple antennae are used within a patient simultaneously or in series (e.g., switching) to deliver energy of a desired intensity and geometry within the patient. In some embodiments, the antennas are individually controllable. In some embodiments, the multiple antennas may be operated by a single user, by a computer, or by multiple users.

In some embodiments, the energy delivery devices having an antenna with an inner conductor and a conductive permanent tip encapsulated in a biocompatible material are designed to operate within a sterile field. The present invention is not limited to a particular sterile field setting. In some embodiments, the sterile field includes a region surrounding a subject (e.g., an operating table). In some embodiments, the sterile field includes any region permitting access only to sterilized items (e.g., sterilized devices, sterilized accessory agents, sterilized body parts). In some embodiments, the sterile field includes any region vulnerable to pathogen infection. In some embodiments, the sterile field has therein a sterile field barrier establishing a barrier between a sterile field and a non-sterile field. The present invention is not limited to a particular sterile field barrier. In some embodiments, the sterile field barrier is the drapes surrounding a subject undergoing a procedure involving use of the energy delivery devices of the present invention (e.g., tissue ablation). In some embodiments, a room is sterile and provides the sterile field. In some embodiments, the sterile field barrier is established by a user of the systems of the present invention (e.g., a physician). In some embodiments, the sterile field barrier hinders entry of non-sterile items into the sterile field. In some embodiments, the energy delivery is provided in the sterile field, while one or more other components of the system (e.g., the power supply) are not contained in the sterile field.

In some embodiments, the energy delivery devices have therein protection sensors designed to prevent undesired use of the energy delivery devices. The energy delivery devices are not limited to a particular type or kind of protection sensors. In some embodiments, the energy delivery devices have therein a temperature sensor designed to measure the temperature of, for example, the energy delivery device and/or the tissue contacting the energy delivery device. In some embodiments, as a temperature reaches a certain level the sensor communicates a warning to a user via, for example, the processor. In some embodiments, the energy delivery devices have therein a skin contact sensor designed to detect contact of the energy delivery device with skin (e.g., an exterior surface of the skin). In some embodiments, upon contact with undesired skin, the skin contact sensor communicates a warning to a user via, for example, the processor. In some embodiments, the energy delivery devices have therein an air contact sensor designed to detect contact of the energy delivery device with ambient air (e.g., detection through measurement of reflective power of electricity passing through the device). In some embodiments, upon contact with undesired air, the skin contact sensor communicates a warning to a user via, for example, the processor. In some embodiments, the sensors are designed to prevent use of the energy delivery device (e.g., by automatically reducing or preventing power delivery) upon detection of an undesired occurrence (e.g., contact with skin, contact with air, undesired temperature increase/decrease). In some embodiments, the sensors communicate with the processor such that the processor displays a notification (e.g., a green light) in the absence of an undesired occurrence. In some embodiments, the sensors communicate with the processor such that the processor displays a notification (e.g., a red light) in the presence of an undesired occurrence and identifies the undesired occurrence.

In some embodiments, the energy delivery devices having an antenna with an inner conductor and a conductive permanent tip encapsulated in a biocompatible material are capable for use above a manufacturer's recommended power rating. In some embodiments, the energy delivery devices having therein cooling techniques rendering the devices capable of higher power delivery. The present invention is not limited to a particular amount of power increase. In some embodiments, power ratings exceed manufacturer's recommendation by 5× or more (e.g., 5×, 6×, 10×, 15×, 20×, etc.).

In addition, the devices of the present invention are configured to deliver energy from different regions of the device (e.g., outer conductor segment gaps) at different times (e.g., controlled by a user) and at different energy intensities (e.g., controlled by a user). Such control over the device permits the phasing of energy delivery fields for purposes of achieving constructive phase interference at a particular tissue region or destructive phase interference at a particular tissue region. For example, a user may employ energy delivery through two (or more) closely positioned outer conductor segments so as to achieve a combined energy intensity (e.g., constructive phase interference). Such a combined energy intensity may be useful in particularly deep or dense tissue regions. In addition, such a combined energy intensity may be achieved through utilization of two (or more) devices. In some embodiments, phase interference (e.g., constructive phase interference, destructive phase interference), between one or more devices, is controlled by a processor, a tuning element, a user, and/or a power splitter. Thus, the user is able to control the release of energy through different regions of the device and control the amount of energy delivered through each region of the device for purposes of precisely sculpting an ablation zone.

The present invention provides a wide variety of methods for cooling the devices. Some embodiments employ meltable barriers that, upon melting, permit the contact of chemicals that carry out an endothermic reaction.

In some embodiments, the device further comprises an anchoring element for securing the antenna at a particular tissue region. The device is not limited to a particular type of anchoring element. In some embodiments, the anchoring element is an inflatable balloon (e.g., wherein inflation of the balloon secures the antenna at a particular tissue region). An additional advantage of utilizing an inflatable balloon as an anchoring element is the inhibition of blood flow or air flow to a particular region upon inflation of the balloon. Such air or blood flow inhibition is particularly useful in, for example, cardiac ablation procedures and ablation procedures involving lung tissue, vascular tissue, and gastrointestinal tissue. In some embodiments, the anchoring element is an extension of the antenna designed to engage (e.g., latch onto) a particular tissue region. Further examples include, but are not limited to, the anchoring elements described in U.S. Pat. Nos. 6,364,876, and 5,741,249. In some embodiments, the anchoring element has a circulating agent (e.g. a gas delivered at or near its critical point; $CO_2$) that freezes the interface between antenna and tissue thereby sticking the antenna in place. In such embodiments, as the tissue melts the antenna remains secured to the tissue region due to tissue desiccation.

Thus, in some embodiments, the devices of the present invention are used in the ablation of a tissue region having high amounts of air and/or blood flow (e.g., lung tissue, cardiac tissue, gastrointestinal tissue, vascular tissue). In some embodiments involving ablation of tissue regions having high amounts of air and/or blood flow, an element is further utilized for inhibiting the air and/or blood flow to that tissue region. The present invention is not limited to a particular air and/or blood flow inhibition element. In some embodiments, the device is combined with an endotracheal/endobronchial tube. In some embodiments, a balloon attached with the device may be inflated at the tissue region for purposes of securing the device(s) within the desired tissue region, and inhibiting blood and/or air flow to the desired tissue region.

In some embodiments, the energy delivery devices have therein a plug region designed to separate interior portion of the energy delivery device so as to, for example, prevent cooling or heating of a portion or portions of the device while permitting cooling or heating of other portions. The plug region may be configured to segregate any desired region or regions of an energy delivery device from any other. In some embodiments, the plug region is designed to prevent cooling of one or more regions of an energy delivery device. In some embodiments, the plug region is designed to prevent cooling of the portion of the energy delivery device configured to deliver ablative energy. The plug region is not limited to a particular manner of preventing cooling of a portion of the device. In some embodiments, the plug region is designed to be in contact with a region having a reduced temperature (e.g., a region of the energy delivery device having circulated coolant). In some embodiments, the material of the plug region is such that it is able to be in contact with a material or region having a low temperature without having its temperature significantly reduced (e.g., an insulating material). The plug region is not limited to a particular type of insulating material (e.g., a synthetic polymer (e.g., polystyrene, polyicynene, polyurethane, polyisocyanurate), aerogel, fibre-glass, cork). The plug region is not limited to particular size dimensions. In some embodiments, the size of the plug region is such that it is able to prevent the cooling effect of a circulating coolant from reducing the temperature of other regions of the energy delivery device. In some embodiments, the plug region is positioned along the entire cannula portion of an energy delivery device. In some embodiments, the plug region is positioned at a distal portion of the cannula portion of an energy delivery device. In some embodiments, the plug region wraps around the external portion of the cannula portion of an energy delivery device.

In some embodiments, the energy delivery devices have therein a "stick" region designed for securing the energy delivery device to a tissue region. The stick region is not limited to a particular manner of facilitating association of an energy delivery device to a tissue region. In some embodiments, the stick region is configured to attain and maintain a reduced temperature such that upon contact with a tissue region, the tissue region adheres to the stick region thereby resulting in attachment of the energy delivery device with the tissue region. The stick region is not limited to a particular material composition. In some embodiments, the stick region is, for example, a metal material, a ceramic material, a plastic material, and/or any combination of such substances. In some embodiments, the stick region comprises any kind of material able to attain and maintain a temperature such that upon contact with a tissue region induces adherence of the tissue region onto the stick region. The stick region is not limited to particular size dimensions. In some embodiments, the size of the stick region is such that it is able to maintain adherence of a tissue region during simultaneous tissue ablation and/or simultaneous movement (e.g., positioning) of the energy delivery device. In some embodiments, two or more stick regions are provided. In some embodiments, the stick region is prevented from exposure to the distal region of the device with a seal. In some embodiments, the seal is positioned between the stick region and the distal region of the device thereby preventing exposure of the stick region to the distal region. In some embodiments, the seal is configured in an air/gas tight manner. In some embodiments, the seal is a laser welding onto the device (e.g., coaxial region). In some embodiments, the seal is induction soldered to the device (e.g., coaxial region). In some embodiments, the seal is partial (e.g., 60%/40%; 55%/45%; 50%/50%) laser welding and induction soldering.

In some embodiments the energy delivery devices having an antenna with an inner conductor and a conductive permanent tip encapsulated in a biocompatible material are configured for delivery of microwave energy with an optimized characteristic impedance (see, e.g., U.S. patent application Ser. No. 11/728,428). Such devices are configured to operate with a characteristic impedance higher than 50 Ω. (e.g., between 50 and 90 Ω; e.g., higher than 50, . . . , 55, 56, 57, 58, 59, 60, 61, 62, . . . 90 Ω., preferably at 77 Ω.).

In some embodiments, the energy delivery devices having an antenna with an inner conductor and a conductive permanent tip encapsulated in a biocompatible material further have coolant passage channels (see, e.g., U.S. Pat. No. 6,461,351, and U.S. patent application Ser. No. 11/728,460). In particular, the energy delivery systems of the present invention utilize devices with coaxial transmission lines that allow cooling by flowing a cooling material through the dielectric and/or the inner or outer conductor of the coaxial component. In some embodiments, the devices are configured to minimize the diameter of the device, while permitting the passage of the coolant. This is accomplished, in some embodiments, by replacing strips of the inner or outer conductor and/or solid dielectric material with channels through which a coolant is transferred. In some embodiments, the channels are generated by stripping the outer or inner conductor and/or solid dielectric material along the length of the coaxial cable from one or more (e.g., two, three, four) zones. With the removed portions of the outer or inner conductor and/or solid dielectric material creating channels for transfer of the coolant, the stripped component fits within a smaller outer conductor than it did prior to removal of the outer or inner conductor and/or solid dielectric material. This provides for smaller devices with all of the advantages derived therefrom. In some embodiments where multiple channels are employed, coolant transfer may be in alternative directions through one or more of the channels. An advantage of such devices is that the diameter of the coaxial cable does not need to be increased to accommodate coolant. This permits the use of cooled devices that are minimally invasive and permit access to regions of a body that are otherwise inaccessible or accessible only with undesired risk. The use of coolant also permits greater energy delivery and/or energy deliver for prolonged periods of time.

In some embodiments, the energy delivery devices having an antenna with an inner conductor and a conductive permanent tip encapsulated in a biocompatible material employ a center fed dipole component (see, e.g., U.S. patent application Ser. No. 11/728,457). The devices are not limited to particular configurations. In some embodiments, the devices have therein a center fed dipole for heating a tissue region through application of energy (e.g., microwave energy). In some embodiments, such devices have a coaxial cable connected to a hollow tube (e.g., where the interior diameter is at least 50% of the exterior diameter; e.g., where the interior diameter is substantially similar to the exterior diameter). The coaxial cable may be a standard coaxial cable, or it may be a coaxial cable having therein a dielectric component with a near-zero conductivity (e.g., air). The hollow tube is not limited to a particular design configuration. In some embodiments, the hollow tube assumes the shape of (e.g., diameter of), for example, a 20-gauge needle. Preferably, the hollow tube is made of a solid, rigid conductive material (e.g., any number of metals, conductor-coated ceramics or polymers, etc.). In some embodiments, the hollow tube is configured with a sharpened point or the addition of a stylet on its distal end to permit direct insertion of the device into a tissue region without the use of, for example, a cannula. The hollow tube is not limited to a particular composition (e.g., metal, plastic, ceramic). In some embodiments, the hollow tube comprises, for example, copper or copper alloys with other hardening metals, silver or silver alloys with other hardening metals, gold-plated copper, metal-plated Macor (machinable ceramic), metal-plated hardened polymers, and/or combinations thereof. The stylet tip may be made of any material. In some embodiments, the tip is made from hardened resin. In some embodiments, the tip is metal. In some embodiments, the stylet tip is made from titanium or an equivalent of titanium. In some embodiments, the stylet tip is braised to zirconia or an equivalent of zirconia. In some such embodiments, the metal tip is an extension of a metal portion of an antenna and is electrically active.

In some embodiments the energy delivery devices having an antenna with an inner conductor and a conductive permanent tip encapsulated in a biocompatible material further have a linear array of antennae components (see, e.g., U.S. Provisional Patent Application No. 60/831,055). The devices are not limited to particular configurations. In some embodiments, the energy delivery devices having a linear array of antennae components have therein an antenna comprising an inner conductor and an outer conductor, wherein the outer conductor is provided in two or more linear segments separated by gaps, such that the length and position of the segments is configured for optimized delivery of energy at the distal end of the antenna. For example, in some embodiments, an antenna comprises a first segment of outer conductor that spans the proximal end of the antenna to a region near the distal end and a second segment of outer conductor distal to the first segment wherein a gap separates or partially separates the first and second segments. The gaps may entirely circumscribe the outer conductor or may only partially circumscribe the outer conductor. In some embodiments, the length of the second segment is $\lambda/2$, $\lambda/4$, etc., although the present invention is not so limited. In some embodiments one or more additional (e.g., third, fourth, fifth) segments are provided distal to the second segment, each of which is separated from the other by a gap. In some embodiments, the antenna is terminated with a conductive terminal end that is in electronic communication with the inner conductor. In some embodiments, the conductive terminal end comprises a disc having a diameter substantially identical to the diameter of the outer conductor. Such antennae provide multiple peaks of energy delivery along the length of the distal end of the antenna, providing a broader region of energy delivery to target larger regions of tissue. The location and position of the peaks is controlled by selecting the length of the outer conductor segments and by controlling the amount of energy delivered.

In some embodiments, the energy delivery devices have precision antennas or precision probes for coupling with an existing antenna.

The precision probes are not limited to coupling with a particular type of antenna. In some embodiments, the antenna has an inner conductor. In some embodiments, the antenna is a triaxial antenna (see, e.g., U.S. Pat. No. 7,101,369; see, also, U.S. patent application Ser. Nos. 10/834,802, 11/236,985, 11/237,136, 11,237,430, 11/440,331, 11/452,637, 11/502,783, 11/514,628; and International Patent Application No. PCT/US05/14534). In some embodiments, the antenna is a coaxial antenna. In some embodiments, the antenna is any type of device configured to deliver (e.g., emit) energy (e.g., ablation device, surgical device, etc.) (see, e.g., U.S. Pat. Nos. 7,101,369, 7,033,352, 6,893,436, 6,878,147, 6,823,218, 6,817,999, 6,635,055, 6,471,696, 6,383,182, 6,312,427, 6,287,302, 6,277,113, 6,251,128, 6,245,062, 6,026,331, 6,016,811, 5,810,803, 5,800,494, 5,788,692, 5,405,346, 4,494,539, U.S. patent application Ser. Nos. 11/728,460, 11/728,457, 11/728,428, 11/237,136, 11/236,985, 10/980,699, 10/961,994, 10/961,761, 10/834, 802, 10/370,179, 09/847,181; Great Britain Patent Application Nos. 2,406,521, 2,388,039; European Patent No. 1395190; and International Patent Application Nos. WO 06/008481, WO 06/002943, WO 05/034783, WO 04/112628, WO 04/033039, WO 04/026122, WO 03/088858, WO 03/039385 WO 95/04385)

The precision probes are not limited to a particular shape and/or design. In some embodiments, the shape of the precision probe is such that it is able to be fitted over the inner conductor of an antenna. In some embodiments, the shape and/or design of the precision probe is cylindrical. In some embodiments, the shape and/or design of the precision probe is tubular.

The precision probes are not limited to a particular positioning within an antenna. In some embodiments, so as to accommodate a precision probe, the outer conductor and dielectric of an antenna is removed so as to generate a portion along the inner conductor wherein the precision probe will be positioned (e.g., thereby generating an exposed inner conductor region). In some such embodiments, a precision probe is positioned along the entire exposed inner conductor region. In some such embodiments, an antenna sleeve (e.g., a polyfluorothetraethylene or PTFE antenna sleeve) is positioned along a portion of the exposed inner conductor and a precision probe positioned along the remaining portion of the exposed inner conductor.

The conductive fitting of the precision probes are not limited to a particular manner of coupling with the inner conductor of an antenna. In some embodiments, the fitting is soldered to an inner conductor. In some embodiments, the fitting is brazed to an inner conductor. In some embodiments, the fitting is crimped to an inner conductor. In some embodiments, the fitting is welded to an inner conductor. In some embodiments, the attachment between the precision probe and inner conductor is electrically conductive.

The precision probes are not limited to particular size dimensions. In some embodiments, the size dimensions of the precision probes are configured to accommodate any type or size of antenna (e.g., inner conductor or an antenna). In some embodiments, the diameter size of the precision probe is as large as possible so as to minimize impedance formed within an outer trocar cap.

In some embodiments, systems are provided which include one or more energy delivery devices and processors that monitor and/or control and/or provide feedback concerning one or more of the components of the system. In some embodiments, the processor is provided within a computer module. The computer module may also comprise software that is used by the processor to carry out one or more of its functions. For example, in some embodiments, the systems of the present invention provide software for regulating the amount of microwave energy provided to a tissue region through monitoring one or more characteristics of the tissue region including, but not limited to, the size and shape of a target tissue, the temperature of the tissue region, and the like (e.g., through a feedback system) (see, e.g., U.S. patent application Ser. Nos. 11/728,460, 11/728,457, and 11/728,428). In some embodiments, the software is configured to provide information (e.g., monitoring information) in real time. In some embodiments, the software is configured to interact with the energy delivery systems of the present invention such that it is able to raise or lower (e.g., tune) the amount of energy delivered to a tissue region. In some embodiments, the software is designed to prime coolants for distribution into, for example, an energy delivery device such that the coolant is at a desired temperature prior to use of the energy delivery device. In some embodiments, the type of tissue being treated (e.g., liver) is inputted into the software for purposes of allowing the processor to regulate (e.g., tune) the delivery of microwave energy to the tissue region based upon pre-calibrated methods for that particular type of tissue region. In other embodiments, the processor generates a chart or diagram based upon a particular type of tissue region displaying characteristics useful to a user of the system. In some embodiments, the processor provides energy delivering algorithms for purposes of, for example, slowly ramping power to avoid tissue cracking due to rapid out-gassing created by high temperatures. In some embodiments, the processor allows a user to choose power, duration of treatment, different treatment algorithms for different tissue types, simultaneous application of power to the antennas in multiple antenna mode, switched power delivery between antennas, coherent and incoherent phasing, etc. In some embodiments, the processor is configured for the creation of a database of information (e.g., required energy levels, duration of treatment for a tissue region based on particular patient characteristics) pertaining to ablation treatments for a particular tissue region based upon previous treatments with similar or dissimilar patient characteristics. In some embodiments, the processor is operated by remote control.

In some embodiments, the processor is used to generate, for example, an ablation chart based upon entry of tissue characteristics (e.g., tumor type, tumor size, tumor location, surrounding vascular information, blood flow information, etc.). In such embodiments, the processor could direct placement of the energy delivery device so as to achieve desired ablation based upon the ablation chart.

In some embodiments a software package is provided to interact with the processor that allows the user to input parameters of the tissue to be treated (e.g., type of tumor or tissue section to be ablated, size, where it is located, location of vessels or vulnerable structures, and blood flow information) and then draw the desired ablation zone on a CT or other image to provide the desired results. The probes may be placed into the tissue, and the computer generates the expected ablation zone based on the information provided. Such an application may incorporate feedback. For example, CT, MRI, or ultrasound imaging or thermometry may be used during the ablation. This data is fed back into the computer, and the parameters readjusted to produce the desired result.

In some embodiments, user interface software is provided for monitoring and/or operating the components of the energy delivery systems. In some embodiments, the user interface software is operated by a touch screen interface. In some embodiments, the user interface software may be implemented and operated within a sterile setting (e.g., a procedure room) or in a non-sterile setting. In some embodiments, the user interface software is implemented and operated within a procedure device hub (e.g., via a processor). In some embodiments, the user interface software is implemented and operated within a procedure cart (e.g., via a processor). The user interface software is not limited to particular functions. Examples of functions associated with the user interface software include, but are not limited to, tracking the number of uses per component within the energy delivery system (e.g., tracking the number of times an energy delivery device is used), providing and tracking real time temperatures of each component or parts of each component (e.g., providing real time temperature of different locations along an energy delivery device (e.g., at the handle, at the stick, at the tip)) (e.g., providing real time temperature of the cables associated with the energy delivery systems), providing and tracking real time temperature of the tissue being treated, providing an automatic shut off for the part or all of the energy delivery system (e.g., an emergency shut off), generation of reports based upon the data accumulated, for example, prior to, during and after a procedure, providing audible and/or visual alerts to a user (e.g., alerts indicating a procedure has begun and/or is finished, alerts indicating a temperature has reached an aberrant level, alerts indicating the length of the procedure has gone beyond a default, etc.).

As used herein, the terms "computer memory" and "computer memory device" refer to any storage media readable by a computer processor. Examples of computer memory include, but are not limited to, random access memory (RAM), read-only memory (ROM), computer chips, optical discs (e.g., compact discs (CDs), digital video discs (DVDs), etc.), magnetic disks (e.g., hard disk drives (HDDs), floppy disks, ZIP.® disks, etc.), magnetic tape, and solid state storage devices (e.g., memory cards, "flash" media, etc.).

As used herein, the term "computer readable medium" refers to any device or system for storing and providing information (e.g., data and instructions) to a computer processor. Examples of computer readable media include, but are not limited to, optical discs, magnetic disks, magnetic tape, solid-state media, and servers for streaming media over networks. As used herein, the terms "processor" and "central processing unit" or "CPU" are used interchangeably and refer to a device that is able to read a program from a computer memory device (e.g., ROM or other computer memory) and perform a set of steps according to the program.

In some embodiments, systems are provided including one or more energy delivery devices and imaging systems comprising imaging devices. The energy delivery systems are not limited to particular types of imaging devices (e.g., endoscopic devices, stereotactic computer assisted neurosurgical navigation devices, thermal sensor positioning systems, motion rate sensors, steering wire systems, intraprocedural ultrasound, interstitial ultrasound, microwave imaging, acoustic tomography, dual energy imaging, fluoroscopy, computerized tomography magnetic resonance imaging, nuclear medicine imaging devices triangulation imaging, thermoacoustic imaging, infrared and/or laser imaging, electromagnetic imaging) (see, e.g., U.S. Pat. Nos. 6,817,976, 6,577,903, and 5,697,949, 5,603,697, and International Patent Application No. WO 06/005,579). In some embodiments, the systems utilize endoscopic cameras, imaging components, and/or navigation systems that permit or assist in placement, positioning, and/or monitoring of any of the items used with the energy systems of the present invention.

In some embodiments, the energy delivery systems provide software configured for use of imaging equipment (e.g., CT, MRI, ultrasound). In some embodiments, the imaging equipment software allows a user to make predictions based upon known thermodynamic and electrical properties of tissue, vasculature, and location of the antenna(s). In some embodiments, the imaging software allows the generation of a three-dimensional map of the location of a tissue region (e.g., tumor, arrhythmia), location of the antenna(s), and to generate a predicted map of the ablation zone.

In some embodiments, the imaging systems of the present invention are used to monitor ablation procedures (e.g., microwave thermal ablation procedures, radio-frequency thermal ablation procedures). The present invention is not limited to a particular type of monitoring. In some embodiments, the imaging systems are used to monitor the amount of ablation occurring within a particular tissue region(s) undergoing a thermal ablation procedure. In some embodiments, the monitoring operates along with the ablation devices (e.g., energy delivery devices) such that the amount of energy delivered to a particular tissue region is dependent upon the imaging of the tissue region. The imaging systems are not limited to a particular type of monitoring. The present invention is not limited to what is being monitored with the imaging devices. In some embodiments, the monitoring is imaging blood perfusion for a particular region so as to detect changes in the region, for example, before, during and after a thermal ablation procedure. In some embodiments, the monitoring includes, but is not limited to, MRI imaging, CT imaging, ultrasound imaging, nuclear medicine imaging, and fluoroscopy imaging. For example, in some embodiments, prior to a thermal ablation procedure, a contrast agent (e.g., iodine or other suitable CT contrast agent; gadolinium chelate or other suitable MRI contrast agent, microbubbles or other suitable ultrasound constrast agent, etc.) is supplied to a subject (e.g., a patient) and the contrast agent perfusing thorugh a particular tissue region that is undergoing the ablation procedure is monitored for blood perfusion changes. In some embodiments, the monitoring is qualitative information about the ablation zone properties (e.g., the diameter, the length, the cross-sectional area, the volume). The imaging system is not limited to a particular technique for monitoring qualitative information. In some embodiments, techniques used to monitor qualitative information include, but are not limited to, non-imaging techniques (e.g., time-domain reflectometry, time-of-flight pulse detection, frequency-modulated distance detection, eigenmode or resonance frequency detection or reflection and transmission at any frequency, based on one interstitial device alone or in cooperation with other interstitial devices or external devices). In some embodiments, the interstitial device provides a signal and/or detection for imaging (e.g., electro-acoustic imaging, electromagnetic imaging, electrical impedance tomography). In some embodiments, non-imaging techniques are used to monitor the dielectric properties of the medium surrounding the antenna, detect an interface between the ablated region and normal tissue through several means, including resonance frequency detection, reflectometry or distance-finding techniques, power reflection/transmission from interstitial antennas or external antennas, etc. In some embodiments, the qualitative information is an estimate of ablation status, power delivery status, and/ or simple go/no-go checks to ensure power is being applied.

In some embodiments, the imaging systems are designed to automatically monitor a particular tissue region at any desired frequency (e.g., per second intervals, per one-minute intervals, per ten-minute intervals, per hour-intervals, etc.). In some embodiments, the present invention provides software designed to automatically obtain images of a tissue region (e.g., MRI imaging, CT imaging, ultrasound imaging, nuclear medicine imaging, fluoroscopy imaging), automatically detect any changes in the tissue region (e.g., blood perfusion, temperature, amount of necrotic tissue, etc.), and based on the detection to automatically adjust the amount of energy delivered to the tissue region through the energy delivery devices. Likewise, an algorithm may be applied to predict the shape and size of the tissue region to be ablated (e.g., tumor shape) such that the system recommends the type, number, and location of ablation probes to effectively treat the region. In some embodiments, the system is configured to with a navigation or guidance system (e.g., employing triangulation or other positioning routines) to assist in or direct the placement of the probes and their use.

For example, such procedures may use the enhancement or lack of enhancement of a contrast material bolus to track the progress of an ablation or other treatment procedure. Subtraction methods may also be used (e.g., similar to those used for digital subtraction angiography). For example, a first image may be taken at a first time point. Subsequent images subtract out some or all of the information from the first image so that changes in tissue are more readily observed. Likewise, accelerated imaging techniques may be used that apply "under sampling" techniques (in constrast to Nyquist sampling). It is contemplated that such techniques provide excellent signal-to-noise using multiple low resolutions images obtained over time. For example, an algorithm called HYPER (highly constrained projection reconstruction) is available for MRI that may be applied to embodiments of the systems of the invention.

As thermal-based treatments coagulate blood vessels when tissue temperatures exceed, for example, 50° C., the coagulation decreases blood supply to the area that has been completely coagulated. Tissue regions that are coagulated do not enhance after the administration of contrast. In some embodiments, the present invention utilizes the imaging systems to automatically track the progress of an ablation procedure by giving, for example, a small test injection of contrast to determine the contrast arrival time at the tissue region in question and to establish baseline enhancement. In some embodiments, a series of small contrast injections is next performed following commencement of the ablation procedure (e.g., in the case of CT, a series of up to fifteen 10 ml boluses of 300 mgI/ml water soluble contrast is injected), scans are performed at a desired appropriate post-injection time (e.g., as determined from the test injection), and the contrast enhancement of the targeted area is determined using, for example, a region-of-interest (ROI) to track any one of a number of parameters including, but not limited to, attenuation (Hounsfield Units [HU]) for CT, signal (MRI), echogenicity (ultrasound), etc. The imaged data is not limited to a particular manner of presentation. In some embodiments, the imaging data is presented as color-coded or grey scale maps or overlays of the change in attenuation/signal/echogenicity, the difference between targeted and non-targeted tissue, differences in arrival time of the contrast bolus during treatment, changes in tissue perfusion, and any other tissue properties that can be measured before and after the injection of contrast material. The methods of the present invention are not limited to selected ROI's, but can be generalized to all pixels within any image. The pixels can be color-coded, or an overlay used to demonstrate where tissue changes have occurred and are occurring. The pixels can change colors (or other properties) as the tissue property changes, thus giving a near real-time display of the progress of the treatment. This method can also be generalized to 3d/4d methods of image display.

In some embodiments, the area to be treated is presented on a computer overlay, and a second overlay in a different color or shading yields a near real-time display of the progress of the treatment. In some embodiments, the presentation and imaging is automated so that there is a feedback loop to a treatment technology (RF, MW, HIFU, laser, cryo, etc) to modulate the power (or any other control parameter) based on the imaging findings. For example, if the perfusion to a targeted area is decreased to a target level, the power could be decreased or stopped. For example, such embodiments are applicable to a multiple applicator system as the power/time/frequency/duty cycle, etc. is modulated for each individual applicator or element in a phased array system to create a precisely sculpted zone of tissue treatment. Conversely, in some embodiments, the methods are used to select an area that is not to be treated (e.g., vulnerable structures that need to be avoided such as bile ducts, bowel, etc.). In such embodiments, the methods monitor tissue changes in the area to be avoided, and warn the user (e.g., treating physician) using alarms (e.g., visible and/or audible alarms) that the structure to be preserved is in danger of damage. In some embodiments, the feedback loop is used to modify power or any other parameter to avoid continued damage to a tissue region selected not to be treated. In some embodiments, protection of a tissue region from ablation is accomplished by setting a threshold value such as a target ROI in a vulnerable area, or using a computer overlay to define a "no treatment" zone as desired by the user.

In some embodiments, systems are provided including one or more energy delivery devices and tuning elements for adjusting the amount of energy delivered to the tissue region. In some embodiments, the tuning element is manually adjusted by a user of the system. In some embodiments, a tuning system is incorporated into an energy delivery device so as to permit a user to adjust the energy delivery of the device as desired (see, e.g., U.S. Pat. Nos. 5,957969, 5,405,346). In some embodiments, the device is pretuned to the desired tissue and is fixed throughout the procedure. In some embodiments, the tuning system is designed to match impedance between a generator and an energy delivery device (see, e.g., U.S. Pat. No. 5,364,392). In some embodiments, the tuning element is automatically adjusted and controlled by a processor of the present invention (see, e.g., U.S. Pat. No. 5,693,082). In some embodiments, a processor adjusts the energy delivery over time to provide constant energy throughout a procedure, taking into account any number of desired factors including, but not limited to, heat, nature and/or location of target tissue, size of lesion desired, length of treatment time, proximity to sensitive organ areas or blood vessels, and the like. In some embodiments, the system comprises a sensor that provides feedback to the user or to a processor that monitors the function of the device continuously or at time points. The sensor may record and/or report back any number of properties, including, but not limited to, heat at one or more positions of a components of the system, heat at the tissue, property of the tissue, and the like. The sensor may be in the form of an imaging device such as CT, ultrasound, magnetic resonance imaging, or any other imaging device. In some embodiments, particularly for research application, the system records and stores the information for use in future optimization of the system generally and/or for optimization of energy delivery under particular conditions (e.g., patient type, tissue type, size and shape of target region, location of target region, etc.).

In some embodiments, systems are provided including one or more energy delivery devices and coolant systems so as to reduce undesired heating within and along an energy delivery device (e.g., tissue ablation catheter). The systems of the present invention are not limited to a particular cooling system mechanism. In some embodiments, the systems are designed to circulate a coolant (e.g., air, liquid, etc.) throughout an energy delivery device such that the coaxial transmission line(s) and antenna(e) temperatures are reduced. In some embodiments, the systems utilize energy delivery devices having therein channels designed to accommodate coolant circulation. In some embodiments, the systems provide a coolant sheath wrapped around the antenna or portions of the antenna for purposes of cooling the antenna externally (see, e.g., U.S. patent application Ser. No. 11/053,987). In some embodiments, the systems utilize energy delivery devices having a conductive covering around the antenna for purposes of limiting dissipation of heat onto surrounding tissue (see, e.g., U.S. Pat. No. 5,358, 515). In some embodiments, upon circulation of the coolant, it is exported into, for example, a waste receptacle. In some embodiments, upon circulation of the coolant it is recirculated. In some embodiments, the coolant is a gas circulated at or near its critical point. In some embodiments, the gas delivered at or near its critical point is carbon dioxide gas. In some embodiments, the energy delivery devices are configured to compress transported coolants (e.g., carbon dioxide gas at or near its critical point) at a desired pressure so as to retain the coolant at or near its critical point.

In some embodiments, the systems utilize expandable balloons in conjunction with energy delivery devices for purposes of urging tissue away from the surface of the antenna(e) (see, e.g., U.S. patent application Ser. No. 11/053,987).

In some embodiments, the systems utilize devices configured to attach onto an energy delivery device for purposes of reducing undesired heating within and along the energy delivery device (see, e.g., U.S. patent application Ser. No. 11/237,430).

In some embodiments, systems are provided including one or more energy delivery devices and identification elements (e.g., RFID elements, identification rings (e.g., fidicials), barcodes, etc.) associated with one or more components of the system. In some embodiments, the identification element conveys information about a particular component of the system. The present invention is not limited by the information conveyed. In some embodiments, the information conveyed includes, but is not limited to, the type of component (e.g., manufacturer, size, energy rating, tissue configuration, etc.), whether the component has been used before (e.g., so as to ensure that non-sterile components are not used), the location of the component, patient-specific information and the like. In some embodiments, the information is read by a processor of the present invention. In some such embodiments, the processor configures other components of the system for use with, or for optimal use with, the component containing the identification element.

In some embodiments, the energy delivery devices have thereon one or more markings (e.g., scratches, color schemes, etchings (e.g., laser etchings), painted contrast agent markings, identification rings (e.g., fidicials), and/or ridges) so as to improve identification of a particular energy delivery device (e.g., improve identification of a particular device located in the vicinity of other devices with similar appearances). The markings find particular use where multiple devices are inserted into a patient. In such cases, particularly where the devices may cross each other at various angles, it is difficult for the treating physician to associate which proximal end of the device, located outside of the patient body, corresponds to which distal end of the device, located inside the patient body. In some embodiments, a marking (e.g., a number) a present on the proximal end of the device so that it is viewable by the physician's eyes and a second marking (e.g., that corresponds to the number) is present on the distal end of the device so that it is viewable by an imaging device when present in the body. In some embodiments, where a set of antennas is employed, the individual members of the set are numbered (e.g., 1, 2, 3, 4, etc.) on both the proximal and distal ends. In some embodiments, handles are numbered, a matching numbered detachable (e.g., disposable) antennas are connected to the handles prior to use. In some embodiments, a processor of the system ensures that the handles and antennas are properly matched (e.g., by RFID tag or other means). In some embodiments, where the antenna are disposable, the system provides a warning if a disposable component is attempted to be re-used, when it should have been discarded. In some embodiments, the markings improve identification in any type of detection system including, but not limited to, MRI, CT, and ultrasound detection.

The energy delivery systems of the present invention are not limited to particular types of tracking devices. In some embodiments, GPS and GPS related devices are used. In some embodiments, RFID and RFID related devices are used. In some embodiments, barcodes are used.

In such embodiments, authorization (e.g., entry of a code, scanning of a barcode) prior to use of a device with an identification element is required prior to the use of such a device. In some embodiments, the information element identifies that a components has been used before and sends information to the processor to lock (e.g. block) use of system until a new, sterile component is provided.

In some embodiments, systems are provided including one or more energy delivery devices and temperature monitoring systems. In some embodiments, temperature monitoring systems are used to monitor the temperature of an energy delivery device (e.g., with a temperature sensor). In some embodiments, temperature monitoring systems are used to monitor the temperature of a tissue region (e.g., tissue being treated, surrounding tissue). In some embodiments, the temperature monitoring systems are designed to communicate with a processor for purposes of providing temperature information to a user or to the processor to allow the processor to adjust the system appropriately. In some embodiments, temperatures are monitored at several points along the antenna to estimate ablation status, cooling status or safety checks. In some embodiments, the temperatures monitored at several points along the antenna are used to determine, for example, the geographical characteristics of the ablation zone (e.g., diameter, depth, length, density, width, etc.) (e.g., based upon the tissue type, and the amount of power used in the energy delivery device). In some embodiments, the temperatures monitored at several points along the antenna are used to determine, for example, the status of the procedure (e.g., the end of the procedure). In some embodiments, temperature is monitored using thermocouples or electromagnetic means through the interstitial antenna.

The systems of the present invention (having one or more energy delivery devices having an antenna with an inner conductor and a conductive permanent tip encapsulated in a biocompatible material) may further employ one or more additional components that either directly or indirectly take advantage of or assist the features of the present invention. For example, in some embodiments, one or more monitoring devices are used to monitor and/or report the function of any one or more components of the system. Additionally, any medical device or system that might be used, directly or indirectly, in conjunction with the devices of the present invention may be included with the system. Such components include, but are not limited to, sterilization systems, devices, and components, other surgical, diagnostic, or monitoring devices or systems, computer equipment, handbooks, instructions, labels, and guidelines, robotic equipment, and the like.

In some embodiments, the systems employ pumps, reservoirs, tubing, wiring, and/or other components that provide materials on connectivity of the various components of the systems of the present invention. For example, any type of pump may be used to supply gas or liquid coolants to the antennas of the present invention. Gas or liquid handling tanks containing coolant may be employed in the system. In some embodiments, multiple tanks (e.g., 2, 3, 4, 5, 6, 7, 8, 9, 10, 20, 50, 100, etc.) are used simultaneously, in succession, or as needed. In some embodiments, more than one tank is used such that as one tank becomes empty, additional tanks will be used automatically so as to prevent a disruption in a procedure (e.g., as one $CO_2$ tank is drained empty, a second $CO_2$ tanks is used automatically thereby preventing procedure distruption). In some embodiments wherein $CO_2$ is employed, standard E sized $CO_2$ cylinders are used to supply $CO_2$.

In some embodiments, the systems employ one or more external heating devices. The systems are not limited to a particular use for external heating devices. In some embodiments, the external heating devices are used to retain certain elements of the system within a particular temperature range. For example, in some embodiments, external heating devices are used to retain gas or liquid handling tanks (e.g., tanks containing $CO_2$) providing coolant to one or more devices at within a particular temperature range. Indeed, in some embodiments, external heating devices prevent the natural decreasing in temperature a tank undergoes upon release of its contents thereby assuring that the coolant provided to the device is at a constant temperature or temperature range. The systems are not limited to particular external heating devices. The external heating devices are not limited to a particular manner of retaining the temperature within a particular range. In some embodiments, the external heating devices retain the pressure within a gas or liquid handling tanks (e.g., tanks containing $CO_2$) within a particular range (e.g., heating a tank containing $CO_2$ (e.g., a standard E sized $CO_2$ cylinder) at 1000 pounds per square inch so as to retain the pressure as it releases the $CO_2$ at 850 pounds per square.

In certain embodiments, the energy delivery systems (e.g., the energy delivery devices, the processor, the power supply, the imaging system, the temperature adjustment system, the temperature monitoring system, and/or the identification systems) and all related energy delivery system utilization sources (e.g., cables, wires, cords, tubes, pipes providing energy, gas, coolant, liquid, pressure, and communication items) are provided in a manner that reduces undesired presentation problems (e.g., tangling, cluttering, and sterility compromise associated with unorganized energy delivery system utilization sources). The present invention is not limited to a particular manner of providing the energy delivery systems and energy delivery system utilization sources such that undesired presentation problems are reduced. In some embodiments, energy delivery systems and energy delivery system utilization sources organized with an import/export box, transport sheath, and procedure device pod provide several benefits. Such benefits include, but are not limited to, decreasing the number of cords traversing between a generator (e.g., a microwave generator) and a patient (e.g., decreasing the number of cords on the floor), de-cluttering the sterile environment and procedure room, increasing patient safety by having the energy delivery systems "move" with a patient thereby preventing device dislodgement (e.g., antenna dislodgement), increasing power delivery efficiency by reducing the energy travel distance within the energy delivery device, and reducing disposable costs by shortening the length of the disposable cables.

The present invention is not limited to a particular type or kind of import/export box. In some embodiments, the import/export box contains the power supply and coolant supply. In some embodiments, the import/export box is located outside of a sterile field in which the patient is being treated. In some embodiments, the import/export box is located outside of the room in which the patient is being treated. In some embodiments, the import/export box is located inside of the room in which the patient is being treated and maintained in a sterile manner. In some embodiments, one or more cables connect the import/export box to a procedure device pod. In some embodiments, a single cable is used (e.g., a transport sheath). For example, in some such embodiments, a transport sheath contains components for delivery of both energy and coolant to and/or from the import/export box. In some embodiments, the transport sheath connects to the procedure device pod without causing a physical obstacle for medical practitioners (e.g., travels under the floor, overhead, etc). In some embodiments, the cable is a low-loss cable (e.g., a low-loss cable attaching the power supply to the procedure device hub). In some embodiments, the low-loss cable is secured (e.g., to the procedure device hub, to a procedure table, to a ceiling) so as to prevent injury in the event of accidental pulling of the cable. In some embodiments, the cable connecting the power generator (e.g., microwave power generator) and the procedure device hub is low-loss reusable cable. In some embodiments, the cable connecting the procedure device hub to the energy delivery device is flexible disposable cable. In some embodiments, the cable connecting the procedure device hub to the energy delivery device has high flexibility with "memory" properties (e.g., the cable may be shaped to retain one or more desired positions). In some embodiments, the cable connecting the procedure device hub to the energy delivery device is a silicone covered fiberglass cable.

The present invention is not limited to a particular type or kind of procedure device pod. In some embodiments, the procedure device pod is configured to receive power, coolant, or other elements from the import/export box or other sources. In some embodiments, the procedure device pod provides a control center, located physically near the patient, for any one or more of: delivering energy to a medical device, circulating coolant to a medical device, collecting and processing data (e.g., imaging data, energy delivery data, safety monitoring data, temperature data, and the like), and providing any other function that facilitates a medical procedure. In some embodiments, the procedure device pod is configured to engage the transport sheath so as to receive the associated energy delivery system utilization sources. In some embodiments, the procedure device pod is configured to receive and distribute the various energy delivery system utilization sources to the applicable devices (e.g., energy delivery devices, imaging systems, temperature adjustment systems, temperature monitoring systems, and/or identification systems). For example, in some embodiments, the procedure device pod is configured to receive microwave energy and coolant from energy delivery system utilization sources and distribute the microwave energy and coolant to an energy delivery device. In some embodiments, the procedure device pod is configured to turn on or off, calibrate, and adjust (e.g., automatically or manually) the amount of a particular energy delivery system utilization source as desired. In some embodiments, the procedure device pod has therein a power splitter for adjusting (e.g., manually or automatically turning on, turning off, calibrating) the amount of a particular energy delivery system utilization source as desired. In some embodiments, the procedure device pod has therein software designed to provide energy delivery system utilization sources in a desired manner. In some embodiments, the procedure device pod has a display region indicating associated characteristics for each energy delivery system utilization source (e.g., which devices are presently being used / not used, the temperature for a particular body region, the amount of gas present in a particular $CO_2$ tank, etc.). In some embodiments, the display region has touch capability (e.g., a touch screen). In some embodiments, the processor associated with the energy delivery system is located in the procedure device pod. In some embodiments, the power supply associated with the energy delivery systems is located within the procedure device pod. In some embodiments, the procedure device pod has a sensor configured to automatically inhibit one or more energy delivery system utilization sources upon the occurrence of an undesired event (e.g., undesired heating, undesired leak, undesired change in pressure, etc.). In some embodiments, the weight of the procedure device hub is such that it could be placed onto a patient without causing discomfort and/or harm to the patient (e.g., less than 15 pounds, less than 10 pounds, less than 5 pounds).

The procedure device pods of the present invention are not limited to particular uses or uses within particular settings. Indeed, the procedure device pods are designed for use in any setting wherein the emission of energy is applicable. Such uses include any and all medical, veterinary, and research applications. In addition, the procedure device pods may be used in agricultural settings, manufacturing settings, mechanical settings, or any other application where energy is to be delivered. In some embodiments, the procedure device pods are used in medical procedures wherein patient mobility is not restricted (e.g., CT scanning, ultrasound imaging, etc.).

In some embodiments, the procedure device pod is designed for location within a sterile setting. In some embodiments, the procedure device pod is positioned on a patient's bed (e.g., on the bed; on a railing of the bed), a table that the patient is on (e.g., a table used for CT imaging, ultrasound imaging, MRI imaging, etc.), or other structure near the patient (e.g., the CT gantry). In some embodiments, the procedure device pod is positioned on a separate table. In some embodiments, the procedure device pod is attached to a ceiling. In some embodiments, the procedure device pod is attached to a ceiling such that a user (e.g., a physician) may move it into a desired position (thereby avoiding having to position the energy delivery system utilization sources (e.g., cables, wires, cords, tubes, pipes providing energy, gas, coolant, liquid, pressure, and communication items) on or near a patient while in use). In some embodiments, the procedure device hub is positioned to lay on a patient (e.g., on a patient's legs, thighs, waist, chest). In some embodiments, the procedure device hub is positioned above a patient's head or below a patient's feet. In some embodiments, the procedure device hub has Velcro permitting attachment onto a desired region (e.g., a procedure table, a patient's drape and/or gown).

In some embodiments, the procedure device hub is configured for attachment to a procedure strap used for medical procedures (e.g., a CT safety strap). In some embodiments, the procedure strap attaches to a procedure table (e.g., a CT table) (e.g., through a slot on the sides of the procedure table, through Velcro, through adhesive, through suction) and is used to secure a patient to the procedure table (e.g., through wrapping around the patient and connecting with, for example, Velcro). The procedure device hub is not limited to a particular manner of attachment with a procedure strap. In some embodiments, the procedure device hub is attached to the procedure strap. In some embodiments, the procedure device hub is attached to a separate strap permitting replacement of the procedure strap. In some embodiments, the procedure device hub is attached to a separate strap configured to attach to the procedure strap. In some embodiments, the procedure device hub is attached to a separate strap configured to attach to any region of the procedure table. In some embodiments, the procedure device hub is attached to a separate strap having insulation and/or padding to ensure patient comfort.

In some embodiments, the procedure device hub is configured for attachment to a procedure ring. The present invention is not limited to a particular type or kind of procedure ring. In some embodiments, the procedure ring is configured for placement around a patient (e.g., around a patient's torso, head, feet, arm, etc.). In some embodiments, the procedure ring is configured to attach to a procedure table (e.g., a CT table). The procedure device ring is not limited to a particular shape. In some embodiments, the procedure device ring is, for example, oval, circular, rectangular, diagonal, etc. In some embodiments, the procedure device ring is approximately half of a cyclical shape (e.g., 25% of a cyclical shape, 40% of a cyclical shape, 45% of a cyclical shape, 50% of a cyclical shape, 55 of a cyclical shape, 60 of a cyclical shape, 75 of a cyclical shape). In some embodiments, the procedure ring is, for example, metal, plastic, graphite, wood, ceramic, or any combination thereof. The procedure device hub is not limited to a particular manner of attachment to the procedure ring. In some embodiments, the procedure device hub attaches onto the procedure ring (e.g., with Velcro, with snap-ons, with an adhesive agent). In some embodiments utilizing low-loss cables, the low-loss cables additional attach onto the procedure ring. In some embodiments, the size of the procedure ring can be adjusted (e.g., retracted, extended) to accommodate the size of a patient. In some embodiments, additional items may be attached to the procedure ring. In some embodiments, the procedure ring may be easily moved to and from the vicinity of a patient.

In some embodiments, the procedure device hub is configured for attachment onto a custom sterile drape. The present invention is not limited to a particular type or kind of custom sterile drape. In some embodiments, the custom sterile drape is configured for placement onto a patient (e.g., onto a patient's torso, head, feet, arm, entire body, etc.). In some embodiments, the custom sterile drape is configured to attach to a procedure table (e.g., a CT table). The custom sterile drape is not limited to a particular shape. In some embodiments, the custom sterile drape is, for example, oval, circular, rectangular, diagonal, etc. In some embodiments, the shape of the custom sterile drape is such that it accommodates a particular body region of a patient. In some embodiments, the procedure ring is, for example, cloth, plastic, or any combination thereof. The procedure device hub is not limited to a particular manner of attachment to the custom sterile drape. In some embodiments, the procedure device hub attaches onto the custom sterile drape (e.g., with Velcro, with snap-ons, with an adhesive agent, clamps (e.g., alligator clamps)). In some embodiments utilizing low-loss cables, the low-loss cables additional attach onto the custom sterile drape. In some embodiments, additional items may be attached to the custom sterile drape. In some embodiments, the custom sterile drape may be easily moved to and from the vicinity of a patient. In some embodiments, the custom sterile drape has one more fenestrations for purposes of performing medical procedures.

In some embodiments, the procedure device hub is configured with legs for positioning the hub in the vicinity of a patient. In some embodiments, the procedure device hub has adjustable legs (e.g., thereby allowing positioning of the procedure device hub in a variety of positions). In some embodiments, the procedure device hub has three adjustable legs thereby allowing the device to be positioned in various tri-pod positions. In some embodiments, the legs have therein Velcro permitting attachment onto a desired region (e.g., a procedure table, a patient's drape and/or gown). In some embodiments, the legs are formed from a springy material configured to form an arc over the procedure table (e.g., CT table) and squeeze the rails of the procedure table. In some embodiments, the legs are configured to attach onto the rails of the procedure table.

In some embodiments, the procedure device pod is configured to communicate (wirelessly or via wire) with a processor (e.g., a computer, with the Internet, with a cellular phone, with a PDA). In some embodiments, the procedure device hub may be operated via remote control. In some embodiments, the procedure device pod has thereon one or more lights. In some embodiments, the procedure device hub provides a detectable signal (e.g., auditory, visual (e.g., pulsing light)) when power is flowing from the procedure device hub to an energy delivery device. In some embodiments, the procedure device hub has an auditory input (e.g., an MP3 player). In some embodiments, the procedure device hub has speakers for providing sound (e.g., sound from an MP3 player). In some embodiments, the procedure device hub has an auditory output for providing sound to an external speaker system. In some embodiments, the use of a procedure device pod permits the use of shorter cables, wires, cords, tubes, and/or pipes (e.g., less than 4 feet, 3 feet, 2 feet). In some embodiments, the procedure device pod and/or one more components connected to it, or portions thereof are covered by a sterile sheath. In some embodiments, the procedure device hub has a power amplifier for supplying power (e.g., to an energy delivery device).

In some embodiments, the procedure device pod is configured to compress transported coolants (e.g., $CO_2$) at any desired pressure so as to, for example, retain the coolant at a desired pressure (e.g., the critical point for a gas) so as to improve cooling or temperature maintenance. For example, in some embodiments, a gas is provided at or near its critical point for the purpose of maintaining a temperature of a device, line, cable, or other component at or near a constant, defined temperature. In some such embodiments, a component is not cooled per se, in that its temperature does not drop from a starting temperature (e.g., room temperature), but instead is maintained at a constant temperature that is cooler than where the component would be, but for the intervention. For example, $CO_2$ may be used at or near its critical point (e.g., 31.1 Celsius at 78.21 kPa) to maintain temperature so that components of the system are sufficiently cool enough not to burn tissue, but likewise are not cooled or maintained significantly below room temperature or body temperature such skin in contact with the component freezes or is otherwise damaged by cold. Using such configurations permits the use of less insulation, as there are not "cold" components that must be shielded from people or from the ambient environment. In some embodiments, the procedure device pod has a retracting element designed to recoil used and/or unused cables, wires, cords, tubes, and pipes providing energy, gas, coolant, liquid, pressure, and/or communication items. In some embodiments, the procedure device pod is configured to prime coolants for distribution into, for example, an energy delivery device such that the coolant is at a desired temperature prior to use of the energy delivery device. In some embodiments, the procedure device pod has therein software configured to prime coolants for distribution into, for example, an energy delivery device such that the system is at a desired temperature prior to use of the energy delivery device. In some embodiments, the circulation of coolants at or near critical point permits cooling of the electronic elements of the energy delivery devices without having to use additional cooling mechanisms (e.g., fans).

In one illustrative embodiment, an import/export box contains one or more microwave power sources and a coolant supply (e.g., pressurized carbon dioxide gas). This import/export box is connected to a single transport sheath that delivers both the microwave energy and coolant to a procedure device pod. The coolant line or the energy line within the transport sheath may be wound around one another to permit maximum cooling of the transport sheath itself. The transport sheath is run into the sterile field where a procedure is to take place along the floor in a location that does not interfere with the movement of the medical team attending to the patient. The transport sheath connects to a table located near an imaging table upon which a patient lays. The table is portable (e.g., on wheels) and connectable to the imaging table so that they move together. The table contains arm, which may be flexible or telescoping, so as to permit positioning of the arm above and over the patient. The transport sheath, or cables connected to the transport sheath, run along the arm to the overhead position. At the end of the arm is the procedure device pod. In some embodiments, two or more arms are provided with two or more procedure device pods or two or more sub-components of a single procedure device pod. The procedure device pod is small (e.g., less than 1 foot cube, less than 10 cm cube, etc.) to allow easy movement and positioning above the patient. The procedure device pod contains a processor for controlling all computing aspects of the system. The device pod contains one or more connections ports for connecting cables that lead to energy delivery devices. Cables are connected to the ports. The cables are retractable and less than three feet in length. Use of short cables reduces expense and prevents power loss. When not in use, the cables hang in the air above the patient, out of contact with the patient's body. The ports are configured with a dummy load when not in use (e.g., when an energy delivery device is not connected to a particular port). The procedure device pod is within reach of the treating physician so that computer controls can be adjusted and displayed information can be viewed, in real-time, during a procedure.

In some embodiments, the energy delivery systems utilize procedure carts for maintaining system elements within one area. For example, in some embodiments, the systems provide a procedure cart that is configured to store the cooling supply (e.g., multiple tanks supplying gas or liquid coolant to the devices of the present invention) (e.g., standard E sized $CO_2$ cylinders) for device cooling purposes, external heating devices to maintain the coolant supply at desired pressures, one or more power supplies, one or more related energy delivery system utilization sources (e.g., cables, wires, cords, tubes, pipes providing energy, gas, coolant, liquid, pressure, and communication items), and/or the procedure device hub. Indeed, the procedure cart is not limited to a particular design or purpose. In some embodiments, the procedure cart is configured for use within a sterile setting (e.g., a procedure room) and has therein cooling tanks, related external heating devices, and a procedure device pod / hub. In some embodiments, the procedure cart is configured for non-sterile settings only. In some embodiments, the procedure cart is configured for easy movement (e.g., it is designed with wheels). The procedure cart is configured to connect with any component of the energy delivery systems of the present invention (e.g., the import/export box, the transport sheath, and/or the procedure device hub). In some embodiments, the procedure cart has therein a display region for operating and/or monitoring the components of the energy delivery systems (e.g., user interface software). In some embodiments, the procedure cart is configured to communicate (wirelessly or via wire) with a processor (e.g., a computer, with the Internet, with a cellular phone, with a PDA). In some embodiments, the procedure cart is configured to send and receive information (wirelessly or via wire) pertaining to the energy delivery systems (e.g., the number of uses for each component, which devices are being used, etc.).

The systems of the present invention including energy delivery devices having an antenna with an inner conductor and a conductive permanent tip encapsulated in a biocompatible material are not limited to particular uses. Indeed, the energy delivery systems of the present invention are designed for use in any setting wherein the emission of energy is applicable. Such uses include any and all medical, veterinary, and research applications. In addition, the systems and devices of the present invention may be used in agricultural settings, manufacturing settings, mechanical settings, or any other application where energy is to be delivered.

In some embodiments, the systems are configured for open surgery, percutaneous, intravascular, intracardiac, endoscopic, intraluminal, laparoscopic, or surgical delivery of energy. In some embodiments, the energy delivery devices may be positioned within a patient's body through a catheter, through a surgically developed opening, and/or through a body orifice (e.g., mouth, ear, nose, eyes, vagina, penis, anus) (e.g., a N.O.T.E.S. procedure). In some embodiments, the systems are configured for delivery of energy to a target tissue or region. In some embodiments, a positioning plate is provided so as to improve percutaneous, intravascular, intracardiac, laparoscopic, and/or surgical delivery of energy with the energy delivery systems of the present invention. The present invention is not limited to a particular type and/or kind of positioning plate. In some embodiments, the positioning plate is designed to secure one or more energy delivery devices at a desired body region for percutaneous, intravascular, intracardiac, laparoscopic, and/or surgical delivery of energy. In some embodiments, the composition of the positioning plate is such that it is able to prevent exposure of the body region to undesired heat from the energy delivery system. In some embodiments, the plate provides guides for assisted positioning of energy delivery devices. The present invention is not limited by the nature of the target tissue or region. Uses include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, metastatic tumors. In some embodiments, the device is configured for movement and positioning, with minimal damage to the tissue or organism, at any desired location, including but not limited to, the brain, neck, chest, abdomen, and pelvis. In some embodiments, the systems are configured for guided delivery, for example, by computerized tomography, ultrasound, magnetic resonance imaging, fluoroscopy, and the like.

In certain embodiments, the present invention provides methods of treating a tissue region, comprising providing a tissue region and a system described herein (e.g., an energy delivery device having an antenna with an inner conductor and a conductive permanent tip encapsulated in a biocompatible material, and at least one of the following components: a processor, a power supply, a temperature monitor, an imager, a tuning system, and/or a temperature reduction system); placing the energy delivery device through a sheath (e.g., an endoscopic sheath) such that the conductive permanent tip encapsulated in a biocompatible material does not damage (e.g., scratch, pierce) the sheath to a desired tissue region; melting/dissolving the biocompatible material encapsulating the conductive permanent tip; adjusting the conductive permanent tip to a desired angle and/or position in relation to the energy delivery device antenna; positioning a portion of the energy delivery device in the vicinity of the tissue region, and delivering an amount of energy with the device to the tissue region. In some embodiments, the tissue region is a tumor. In some embodiments, the delivering of the energy results in, for example, the ablation of the tissue region and/or thrombosis of a blood vessel, and/or electroporation of a tissue region. In some embodiments, the tissue region is a tumor. In some embodiments, the tissue region comprises one or more of the heart, liver, genitalia, stomach, lung, large intestine, small intestine, brain, neck, bone, kidney, muscle, tendon, blood vessel, prostate, bladder, and spinal cord.

INCORPORATION BY REFERENCE

The entire disclosure of each of the patent documents and scientific articles referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A system comprising: an energy delivery device having a proximal end and a distal end, wherein the energy delivery device comprises: a) an antenna having a proximal end and a distal end and a fixed width and length, wherein the antenna has a linear shape extending from the proximal end to the distal end, wherein the antenna comprises an inner conductor having an inner conductor proximal end and an inner conductor distal end, and coolant channels for circulating carbon dioxide at or near its critical point from the proximal end of the energy delivery device to the distal end of the energy delivery device; and b) a permanent sharp tip positioned at the distal end of the antenna, wherein the permanent sharp tip is encapsulated in a biocompatible material through exposure of the permanent sharp tip to carbon dioxide gas at or near its critical point circulated from the coolant channels thereby rendering the distal end of the energy delivery device non-sharp, wherein the permanent sharp tip encapsulated in the biocompatible material has a width that is not larger than the width of the antenna, wherein the biocompatible material is any material that in the absence of exposure to carbon dioxide gas at or near its critical point will dissolve resulting in a non-encapsulated permanent tip; and a coolant supply in fluid communication with the coolant channels in the energy delivery device, wherein the coolant supply comprises carbon dioxide; and a control processor configured to regulate the exposure of the permanent sharp tip to carbon dioxide gas at or near its critical point circulated from the coolant channels in order to encapsulate the permanent tip in the biocompatible material.

2. The system of claim 1, wherein the permanent sharp tip is a conductive permanent sharp tip or a non-conductive permanent sharp tip.

3. The system of claim 2, wherein the conductive or non-conductive permanent tip has one or more of the following characteristics:
is cone shaped;
is titanium based;
is coated with a non-stick material;
is fluoropolymer based;
is a beveled needle;
is trifaceted;
is ceramic based;
is high temperature plastic based;
has a diamond like coating;
has micro-serrations;
comprises a trocar.

4. The system of claim 3,
wherein said diamond like coating is a dielectric material,
wherein said diamond like coating is less than 20 microns.

5. The system of claim 3,
wherein said micro-serrations are in a tri-facet or quad-facet design,
wherein said micro-serrations are 50-100 µm in length.

6. The system of claim 3, wherein said conductive permanent tip features a plurality of scales adjacent to said micro-serrations.

7. The system of claim 2,
wherein said inner conductor is not physically coupled to said conductive or non- conductive permanent tip; or
wherein said inner conductor is capactively-coupled to said conductive or non-conductive permanent tip.

8. The system of claim 2, wherein said conductive or non-conductive permanent tip is attached to an insulator, said insulator attached to a distal end of said metal fitting, wherein said insulator comprises a ceramic insulator.

9. The system of claim 8, wherein said metal fitting, insulator, and conductive or non-conductive tip are positioned and dimensioned so as to generate a low impedance overlap to transfer energy to said conductive or non-conductive tip when energy is supplied to said inner conductor.

10. The system of claim 1, wherein the biocompatible material is dome shaped or bullet shaped or cylindrically shaped or consistent with the shape of the antenna.

11. The system of claim 1,
wherein said antenna comprises a conductive outer conductor surrounding at least a portion of said inner conductor,
wherein said antenna comprises a dielectric material between said inner and outer conductors.

12. The system of claim 1, wherein said antenna is a triaxial antenna.

13. The system of claim 1,
wherein said inner conductor comprises a first region distal to a second region, said second region distal to a third region,
wherein said third region is contained in a triaxial antenna wherein the inner conductor is enveloped by a dielectric layer, and the dielectric layer is enveloped by an outer conductor,
wherein said second region lacks the outer conductor of said triaxial antenna,
wherein said first region lacks the outer conductor and the dielectric material of said triaxial antenna,
wherein said first region is adhered to and surrounded by a metal fitting, wherein said metal fitting is a brass metal fitting, wherein said metal fitting extends distally beyond the most distal end of said inner conductor, wherein said metal fitting abuts the dielectric layer surrounding the inner conductor in the second region, wherein said second region comprises a proximal portion containing the dielectric layer of said triaxial antenna and a distal portion lacking said dielectric layer of said triaxial antenna, wherein said distal portion of said second region comprises a non-conductive sleeve surrounding said inner conductor, wherein said non-conductive sleeve comprises PTFE.

14. The system of claim 13, wherein said metal fitting is adhered to said inner conductor via an electrically conductive adhesive.

15. The system of claim 1, further comprising a power supply electrically connected to said device, wherein said power supply generates microwave energy.

16. The system of claim 15, wherein the control processor further regulates energy delivery from said power supply to said antenna.

* * * * *